United States Patent
Klimanskaya et al.

(10) Patent No.: US 9,040,039 B2
(45) Date of Patent: *May 26, 2015

(54) MODALITIES FOR THE TREATMENT OF DEGENERATIVE DISEASES OF THE RETINA

(71) Applicant: Ocata Therapeutics, Inc., Marlborough, MA (US)

(72) Inventors: Irina V. Klimanskaya, Upton, MA (US); Robert P. Lanza, Clinton, MA (US)

(73) Assignee: Ocata Therapeutics, Inc., Marlborough, MA (US)

( * ) Notice: Subject to any disclaimer, the term of this patent is extended or adjusted under 35 U.S.C. 154(b) by 213 days.

This patent is subject to a terminal disclaimer.

(21) Appl. No.: 13/865,751

(22) Filed: Apr. 18, 2013

(65) Prior Publication Data

US 2013/0302288 A1    Nov. 14, 2013

Related U.S. Application Data

(63) Continuation of application No. 13/477,763, filed on May 22, 2012, which is a continuation of application No. 12/857,911, filed on Aug. 17, 2010, now Pat. No. 8,268,303, which is a continuation of application No. 11/041,382, filed on Jan. 24, 2005, now Pat. No. 7,794,704.

(60) Provisional application No. 60/538,964, filed on Jan. 23, 2004.

(51) Int. Cl.
*A61K 35/12* (2006.01)
*C12N 5/0793* (2010.01)
*A61K 35/44* (2006.01)
*A61K 49/00* (2006.01)
*A61P 27/02* (2006.01)
*C12N 5/071* (2010.01)
*C12N 5/079* (2010.01)
*A61K 35/30* (2006.01)
*A61K 35/36* (2006.01)

(52) U.S. Cl.
CPC .............. *C12N 5/0621* (2013.01); *A61K 35/12* (2013.01); *A61K 35/44* (2013.01); *C12N 5/062* (2013.01); *C12N 2500/32* (2013.01); *C12N 2500/44* (2013.01); *C12N 2501/01* (2013.01); *C12N 2501/115* (2013.01); *C12N 2501/15* (2013.01); *C12N 2501/155* (2013.01); *C12N 2501/235* (2013.01); *C12N 2501/33* (2013.01); *C12N 2506/02* (2013.01); *A61K 35/30* (2013.01); *A61K 35/36* (2013.01); *A61K 35/545* (2013.01); *C12N 2501/60* (2013.01)

(58) Field of Classification Search
None
See application file for complete search history.

(56) References Cited

U.S. PATENT DOCUMENTS

| | | |
|---|---|---|
| 6,331,313 B1 | 12/2001 | Wong et al. |
| 6,642,048 B2 | 11/2003 | Xu et al. |
| 7,247,479 B2 | 7/2007 | Kochanek et al. |
| 7,625,582 B2 | 12/2009 | Wong |
| 7,736,896 B2 | 6/2010 | Klimanskaya et al. |
| 7,794,704 B2 | 9/2010 | Klimanskaya et al. |
| 7,795,025 B2 | 9/2010 | Klimanskaya et al. |
| 8,268,303 B2 | 9/2012 | Klimanskaya et al. |
| 2002/0022268 A1 | 2/2002 | Xu et al. |
| 2002/0035735 A1 | 3/2002 | Schatten et al. |
| 2003/0087859 A1 | 5/2003 | Kochanek et al. |
| 2004/0018617 A1 | 1/2004 | Hwang |
| 2004/0086494 A1 | 5/2004 | John |
| 2004/0133095 A1 | 7/2004 | Dunki-Jacobs et al. |
| 2005/0032126 A1 | 2/2005 | Coombs et al. |
| 2006/0002900 A1 | 1/2006 | Binder et al. |
| 2006/0018886 A1 | 1/2006 | Klimanskaya et al. |
| 2006/0031951 A1 | 2/2006 | Klimanskaya |
| 2006/0147437 A1 | 7/2006 | Allen et al. |
| 2007/0031386 A1 | 2/2007 | Klimanskaya |
| 2009/0233324 A1 | 9/2009 | Kopf-Sill |
| 2010/0057056 A1 | 3/2010 | Gurtner et al. |
| 2010/0105100 A1 | 4/2010 | Sakurada et al. |
| 2010/0299765 A1 | 11/2010 | Klimanskaya et al. |
| 2011/0027333 A1 | 2/2011 | Idelson et al. |
| 2011/0117062 A1 | 5/2011 | Klimanskaya et al. |
| 2011/0117063 A1 | 5/2011 | Klimanskaya et al. |

(Continued)

FOREIGN PATENT DOCUMENTS

| | | |
|---|---|---|
| CN | 1449448 A | 10/2003 |
| CN | 101155913 A | 4/2008 |

(Continued)

OTHER PUBLICATIONS

[No Author Listed], A study of implantation of human embryonic stem cell derived retinal pigment epithelium in subjects with acute wet age related macular degeneration and recent rapid vision decline. First received Sep. 19, 2012. Last verified Dec. 2013. NCT01691261 http://clinicaltrials.gov/ct2/show/NCT01691261?term=nct01691261&rank=1 [Accessed Dec. 16, 2013] 3 Pages.

[No Author Listed], ACT confirms Clinical Trial Participant Showed Improvement in Vision Form 20/400 to 20/40 Following Treatment. Press release dated May 16, 2013. http://www.advancedcell.com/news-and-media/press-releases/act-confirms-clinical-trial-participant-showed-improvement-in-vision-from-20-400-to-20-40-following-treatment/index.asp [Last accessed Dec. 16, 2013] 2 Pages.

(Continued)

*Primary Examiner* — Gregory S Emch

(74) *Attorney, Agent, or Firm* — Wolf, Greenfield & Sacks, P.C.

(57) ABSTRACT

This invention relates to methods for improved cell-based therapies for retinal degeneration and for differentiating human embryonic stem cells and human embryo-derived into retinal pigment epithelium (RPE) cells and other retinal progenitor cells.

17 Claims, 12 Drawing Sheets

(56) References Cited

U.S. PATENT DOCUMENTS

| | | |
|---|---|---|
| 2011/0274662 A1 | 11/2011 | Malcuit et al. |
| 2013/0022680 A1 | 1/2013 | Klimanskaya et al. |
| 2013/0149284 A1 | 6/2013 | Malcuit et al. |
| 2013/0195806 A1 | 8/2013 | Gay et al. |
| 2013/0302286 A1 | 11/2013 | Klimanskaya et al. |
| 2013/0302426 A1 | 11/2013 | Klimanskaya et al. |
| 2013/0302824 A1 | 11/2013 | Klimanskaya et al. |
| 2013/0316451 A1 | 11/2013 | Klimanskaya et al. |
| 2013/0316452 A1 | 11/2013 | Klimanskaya et al. |
| 2014/0294779 A1 | 10/2014 | Klimanskaya et al. |
| 2014/0356432 A1 | 12/2014 | Klimanskaya et al. |
| 2015/0086512 A1 | 3/2015 | Malcuit et al. |

FOREIGN PATENT DOCUMENTS

| | | |
|---|---|---|
| JP | 9-501303 | 2/1997 |
| JP | 2002-500202 | 1/2002 |
| JP | 2003-523766 | 8/2003 |
| JP | 2003-530880 | 10/2003 |
| JP | 2007-522131 | 8/2007 |
| WO | WO 94/25569 A1 | 11/1994 |
| WO | WO 98/30679 A1 | 7/1998 |
| WO | WO 99/34834 A1 | 7/1999 |
| WO | WO 99/45094 A1 | 9/1999 |
| WO | WO 01/30978 A1 | 5/2001 |
| WO | WO 01/62899 A2 | 8/2001 |
| WO | WO 01/81551 A2 | 11/2001 |
| WO | WO 02/16620 A2 | 2/2002 |
| WO | WO 03/049773 A1 | 6/2003 |
| WO | WO 03/087368 A2 | 10/2003 |
| WO | WO 2005/070011 A2 | 8/2005 |
| WO | WO 2006/052646 A2 | 5/2006 |
| WO | WO 2006/080952 A2 | 8/2006 |
| WO | WO 2006/085209 A1 | 8/2006 |
| WO | WO 2008/020675 A1 | 2/2008 |
| WO | WO 2008/129554 A1 | 10/2008 |
| WO | WO 2009/050657 A2 | 4/2009 |
| WO | WO 2009/051671 A1 | 4/2009 |
| WO | WO 2011/063005 A2 | 5/2011 |
| WO | WO 2012/012803 A2 | 1/2012 |
| WO | WO 2012/149484 A2 | 11/2012 |
| WO | WO 2013/184809 A1 | 12/2013 |

OTHER PUBLICATIONS

[No Author Listed], Advanced Cell Technology Announces Interim Data from Its Three Ongoing Macular Degeneration Trials. Press release dated Nov. 8, 2012. http://www.advancedcell.com/documents/0000/0427/advanced-cell-technology-announces-interim-data-from-its-three-ongoing-macular-degeneration-trials.pdf [Last Accessed Dec. 16, 2013] 3 Pages.

[No Author Listed], Advanced Cell Technology Receives Approval from Data Safety Monitoring Board (DSMB) to Initiate Treatment of Third Patient Cohort in All Three Clinical Trials. Press release dated Mar. 2013. http://www.advancedcell.com/documents/0000/0449/advanced-cell-technology-receives-approval-from-data-safety-monitoring-board-dsmb-to-initiate-treatment-of-third-patient-cohort-in-all-three-clinical-trials.pdf [Last Accessed Dec. 16, 2013] 3 Pages.

[No Author Listed], New Science Therapeutics: Regenerative Medicine: Cell Replacement Therapy for Age Related Macular Degeneration. Pfizer-Neusentis, 2002-2012. http://www.neusentis.com/KeyPartnershipCaseStudy.php [Last Accessed Dec. 16, 2013] 3 Pages.

Algvere et al., Long-term outcome of RPE allografts in non-immunosuppressed patients with AMD. Eur J Ophthalmol. Jul.-Sep. 1999;9(3):217-30.

Algvere et al., Transplantation of fetal retinal pigment epithelium in age-related macular degeneration with subfoveal neovascularization. Graefes Arch Clin Exp Ophthalmol. Dec. 1994;232(12):707-16.

Amit et al., "Clonally derived human embryonic stem cell lines maintain pluripotency and proliferative potential for prolonged periods of culture," Dev Biol., Nov. 15, 2000;227(2):271-8.

Answers.com. Embryonic Stem Cell. Answers Corp. 2013. http://www.answers.com/topic/embryonic-stem-cell-1. (visited May 12, 2008).

ARPE-19 (ATCC® CRL-2302™) Characteristics. ATCC http://www.atcc.org/products/all/crl-2302.aspx#characteristics [last accessed Mar. 17, 2014].

Binder et al. Transplantation of autologous retinal pigment epithelium in eyes with foveal neovascularization resulting from age-relatedmacular degeneration: a pilot study. Am J Ophthalmol. Feb. 2002;133(2):215-25.

Brederlau, Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.

Brewer et al., Optimized survival of hippocampal neurons in B27-supplemented Neurobasal, a new serum-free medium combination. J Neurosci Res. Aug. 1, 1993;35(5):567-76.

Brunt et al., Stem cells and regenerative medicine—future perspectives. Can J Physiol Pharmacol. Mar. 2012;90(3):327-35. doi:10.1139/y2012-007. Epub Mar. 8, 2012.

Buchholz et al., Derivation of functional retinal pigmented epithelium from induced pluripotent stem cells. Stem Cells. Oct. 2009;27(10):2427-34. doi:10.1002/stem.189.

Carpenter et al., "Enrichment of neurons and neural precursors from human embryonic stem cells," Exp Neural., Dec. 2001;172(2):383-97.

Chaudhry et al., Basal medium composition and serum or serum replacement concentration influences on the maintenance of murine embryonic stem cells. Ctyotechnology (2008) 5:173-9.

Chaum, Tissue Culture Wash Conditions Significantly Alter Gene Expression in Cultured Human Retinal Pigment Epithelial Cells—A Real Time RT—PCR Study (2005), Invest Ophthalmol Vis Sci 2005;46: E-Abstract 3096.

Cock et al., Plasmanate: a new plasma substitute for pediatric therapy. Calif Med. Oct. 1958;89(4):257-9.

Cosgrove, Pigment epithelium-derived factor in idiopathic pulmonary fibrosis: a role in aberrant angiogenesis. Am J Respir Crit Care Med. Aug. 1, 2004;170(3):242-51. Epub Apr. 29, 2004.

Davis et al., "A human retinal pigment epithelial cell line that retains epithelial characteristics after prolonged culture," Invest Ophthalmol Vis Sci., Apr. 1995;36(5):955-64.

Del Priore et al., Survival of allogeneic porcine retinal pigment epithelial sheets after subretinal transplantation. Invest Ophthalmol Vis Sci. Mar. 2004;45(3):985-92.

Dunn et al., "ARPE-19, a human retinal pigment epithelial cell line with differentiated properties," Exp Eye Res., Feb. 1996;62(2):155-69.

Durlu et al., Transplantation of Retinal Pigment Epithelium Using Viable Cryopreserved Cells, Cell Transplantation, vol. 6, No. 2, p. 149-162. 1997.

Duta, The role of bestrophin in airway epithelial ion transport. FEBS Lett. Nov. 19, 2004;577(3):551-4.

Emre et al., A Comparative Analysis of Human Embryonic Stem Cells Cultured in a Variety of Media Conditions. Jan. 1, 2008. 8 Pages. http://www.millipore.com/publications.nsf/a73664f9f981af8c852569b9005b4eee/73159860d3320b8a85257501006111a0/$FILE/an1237en00.pdf [last accessed Dec. 10, 2013].

Faktorovich, Photoreceptor degeneration in inherited retinal dystrophy delayed by basic fibroblast growth factor. Nature. Sep. 6, 1990;347(6288):83-6.

Fuhrmann et al., "Extraocular mesenchyme patterns the optic vesicle during early eye development in the embryonic chick" Development, Nov. 2000;127(21):4599-609.

Gepstein et al. Derivation and potential applications of human embryonic stem cells. Circ Res. Nov. 15, 2002;91(10):866-76.

Gong, Effects of extracellular matrix and neighboring cells on induction of human embryonic stem cells into retinal or retinal pigment epithelial progenitors. Exp Eye Res. Jun. 2008;86(6):957-65. doi: 10.1016/j.exer.2008.03.014. Epub Mar. 28, 2008.

Gouras et al., Invest Ophthalmol Vis Sci. Oct. 2002;43(10):3307-11. Retinal degeneration and RPE transplantation in Rpe65(-/-) mice.

(56) References Cited

OTHER PUBLICATIONS

Guan, Loss of pigment epithelium derived factor expression in glioma progression. J Clin Pathol. Apr. 2003;56(4):277-82.

Hammond, Mechanical culture conditions effect gene expression: gravity-induced changes on the space shuttle. Physiol Genomics. Sep. 8, 2000;3(3):163-73.

Haruta, (2003), The 2nd Japanese Society for Regeneration Medicine, Plenary Convention Program (Abstract).

Haruta, In vitro and in vivo characterization of pigment epithelial cells differentiated from primate embryonic stem cells. Invest Ophthalmol Vis Sci. Mar. 2004;45(3):1020-5.

Haruta, Retinal Pigment Epithelial Cells Differentiated from Primate Embryonic Stem Cells (2003), Invest Ophthalmol Vis Sci., 44:E-Abstract 381.

Hirano et al., "Generation of Structures Formed by Lens and Retinal Cells Differentiating From Embryonic Stem Cells," Developmental Dynamics, Wiley-Liss, Inc., New York, NY, vol. 228, No. 4, Dec. 2003, pp. 664-671.

Ho et al., Reattachment of cultured human retinal pigment epithelium to extracellular matrix and human Bruch's membrane. Invest Ophthalmol Vis Sci. May 1997;38(6):1110-8.

Hoffman et al., Characterization and culture of human embryonic stem cells, Nat Biotechnol. Jun. 2005;23(6):699-708.

Hori et al. "Growth inhibitors promote differentiation of insulin-producing tissue from embryonic stem cells" PNAS Dec. 10, 2002 vol. 99 No. 25 pp. 16105-16110.

Hu et al., "A cell culture medium that supports the differentiation of human retinal pigment epithelium into functionally polarized monolayers," Mol Vis., Feb. 7, 2001;7:14-9.

Idelson, Directed differentiation of human embryonic stem cells into functional retinal pigment epithelium cells. Cell Stem Cell. Oct. 2, 2009;5(4):396-408. doi: 10.1016/j.stem.2009.07.002.

Ikeda et al., Generation of Rx+/Pax6+ neural retinal precursors from embryonic stem cells. Proc Natl Acad Sci U S A. Aug. 9, 2005;102(32):11331-6. Epub Aug. 2, 2005.

Inverardi et al., Ch 56: Cell Transplantation. Transplantation Biology: Cellular and Molecular Aspects. Ed. Tiney et al. Lippincott-Raven Publishers, Philadelphia. 1996: 679-87.

Itskovitz-Eldor et al., Differentiation of human embryonic stem cells into embryoid bodies compromising the three embryonic germ layers. Mol Med. Feb. 2000;6(2):88-95.

Jean, Molecular regulators involved in vertebrate eye development. (1998), Mech. Dev., 76:3-18.

Kanuga, Characterization of genetically modified human retinal pigment epithelial cells developed for in vitro and transplantation studies. (2002), Invest Ophthalmol Vis Sci., 43(2):546-555.

Kawamorita, In vitro differentiation of mouse embryonic stem cells after activation by retinoic acid. (2002), Hum Cell, 15(3):178-82.

Kawasaki et al., "Generation of dopaminergic neurons and pigmented epithelia from primate ES cells by stromal cell-derived inducing activity," Proceedings of the National Academy of Sciences of USA, National Academy of Science, Washington, DC.vol. 99, No. 3, Feb. 2002, pp. 1580-1585.

Kawasaki et al., Induction of midbrain dopaminergic neurons from ES cells by stromal cell-derived inducing activity. Neuron. Oct. 2000;28(1):31-40.

Kehat "Human embryonic stem cells can differentiate into myocytes with structural and functional properties of cardiomyocytes," J Clin Invest., Aug. 2001;108(3):407-14.

Kim et al., (2004), Stem Cells, Keystone Symposia, 2004 Abstract Book, p. 94, Abstract 250.

Klimanskaya Declaration, submitted on Feb. 4, 2010, in the U.S. Appl. No. 11/186,720, pp. 1-5.

Klimanskaya et al., "Derivation and comparative assessment of retinal pigment epithelium from human embryonic stem cells using transcriptomics." Cloning and Stem Cells 6:3, 217-245 2004.

Klimanskaya, (2004), Stem Cells, Keystone Symposia, 2004 Abstract Book, p. 94, Abstract 252.

Klimanskaya, (2009), in Stem Cell Anthology, Bruce M. Carlson, ed., Academic Press, Chapter 28, pp. 335-346.

Klimanskaya, Derive and conquer: sourcing and differentiating stem cells for therapeutic applications.(2008), Nature Reviews Drug Discovery, 7(2):131-42.

Klimanskaya, Retinal pigment epithelium. (2006), Methods in Enzymology, 418:169-194.

Kniazeva et al., Clinical and genetic studies of an autosomal dominant cone-rod dystrophy with features of Stargardt disease. Ophthalmic Genet. Jun. 1999;20(2):71-81.

Lanza et al., Prospects for the use of nuclear transfer in human transplantation. Nat Biotechnol. Dec. 1999;17(12):1171-4.

Lawrence, Schwann cell grafting into the retina of the dystrophic RCS rat limits functional deterioration. Royal College of Surgeons. (2000), Invest., Ophthalmol., & Vis. Sci., 41(2):518-528.

Lu et al., "Generation of functinal hemangioblasts from human embryonic stem cells" Nature Methods, vol. 4 No. 6, Jun. 2007, 501-509.

Lu, Long-term safety and function of RPE from human embryonic stem cells in preclinical models of macular degeneration. (2009), Stem Cells, 27(9):2126-2135.

Lund et al. "Cell Transplantation As A Treatment For Retinal Disease," Progress in Retinal and Eye Research, vol. 20, No. 4, Jul. 2001, pp. 415-449.

Lund et al. "Human embryonic stem cell-derived cells rescue visual function in dystrophic RCS rats," Cloning and Stem Cells 8:3, 189-199, 2006.

Lund et al., Subretinal transplantation of genetically modified human cell lines attenuates loss of visual function in dystrophic rats. Proc Natl Acad Sci U S A. Aug. 14, 2001;98(17):9942-7.

Ma, Identification of RPE65 in transformed kidney cells. (1999), FEBS Lett., 452(3):199-204.

Marmostein et al., "Bestrophin, the product of the Best vitelliform macular dystrophy gene (VMD2), localizes to the basolateral plasma membrane of the retinal pigment epithelium," Proc Natl Acad Sci U S A, Nov. 7, 2000;97(23):12758-63.

Mayerson et al., An improved method for isolation and culture of rate retinal pigment epithelial cells, Invest. Ophthalmol and Vis. Sci. 1985;26:1599-1609.

Motohashi et al. Induction of melanocytes from embryonic stem cells and their therapeutic potential. Pigment Cell Res. Aug. 2006;19(4):284-9.

Muotri, Development of functional human embryonic stem cell-derived neurons in mouse brain. (2005), PNAS, 102(51):18644-18648.

Ohno-Matsui et al., Mol Vis. Aug. 29, 2006;12:1022-32. In vitro and in vivo characterization of iris pigment epithelial cells cultured on amniotic membranes.

Ooto et al., "Induction of the Differentiation of Lentoids from Primate Embryonic Stem Cells," Investigative Opthamology & Visual Science, Association for Research in Vision and Opthamology, vol. 44, No. 6, Jun. 2003, pp. 2689-2693.

Opas et al., Formation of retinal pigment epithelium in vitro by transdifferentiation of neural retina cells. Int J Dev Biol. Jun. 2001;45(4):633-42.

Park, In vitro and in vivo analyses of human embryonic stem cell-derived dopamine neurons. (2005), J. Neurochem., 92:1265-1276.

Radtke et al., Vision change after sheet transplant of fetal retina with retinal pigment epithelium to a patient with retinitis pigmentosa. Arch Ophthalmol. Aug. 2004;122(8):1159-65.

Radtke et al., Vision improvement in retinal degeneration patients by implantation of retina together with retinal pigment epithelium. Am J Ophthalmol. Aug. 2008;146(2):172-182. doi:10.1016/j.ajo.2008.04.009. Epub Jun. 10, 2008.

Reubinoff et al., "Embryonic Stem Cell Lines From Human Blastocysts: Somatic Differentiation in Vitro," Nature Biotechnology, Nature Publishing Group, New York, NY, vol. 18, No. 4, Apr. 2000, pp. 399-404.

Rinaudo, Effects of embryo culture on global pattern of gene expression in preimplantation mouse embryos. (2004), Reproduction, 128(3):301-11.

Saari, Cellular retinaldehyde-binding protein is expressed by oligodendrocytes in optic nerve and brain. (1997), Glia, 21(3):259-68.

(56) References Cited

OTHER PUBLICATIONS

Sauve et al., Preservation of visual responsiveness in the superior colliculus of RCS rats after retinal pigment epithelium cell transplantation. Neuroscience. 2002;114(2):389-401.
Schraermeyer et al., 2001, "Subretinally Transplanted Embryonic Stem Cell Rescue Photoreceptor Cells From Degeneration in the RCS Rats," Cell Transplantation, 10:673-680.
Schuldiner et al., "Effects of eight growth factors on the differentiation of cells derived from human embryonic stem cells," Proc Natl Acad Sci U S A, Oct. 10, 2000;97(21):11307-12.
Schwartz, Lancet Embryonic stem cell trials for macular degeneration: a preliminary report The Lancet, vol. 379, Issue 9817, pp. 713-720. (http://dx.doi.org/10.1016/S0140-6736(12)60028-2, available on-line Jan. 24, 2012).
Skottman, Unique gene expression signature by human embryonic stem cells cultured under serum-free conditions correlates with their enhanced and prolonged growth in an undifferentiated stage. (2006), Stem Cells, 24(1):151-67.
Smith et al., Embryo-derived stem cells: of mice and men. Annu Rev Cell Dev Biol. 2001;17:435-62.
Subramanian, Cell transplantation for the treatment of Parkinson's disease. (2001), Seminars Neurol 21(1):103-115.
Sugino et al., Comparison of FRPE and human embryonic stem cell-derived RPE behavior on aged human Bruch's membrane. Invest Ophthalmol Vis Sci. Jul. 1, 2011;52(8):4979-97. doi: 10.1167/iovs.10-5386.
Takahashi, (2003), Geriatric Medicine, 41(12):1791-1795.
Talecris Biotherapeutics, Plasmanate Product Information Sheet, retrieved from http://www.bdipharma.com/Package%20Insert/Talecris/Plasmanate.sub.--- 01-2005.pdf (last visited Jan. 6, 2011).
Thomson et al. "Embryonic Stem Cell Lines Derived from Human Blastocysts," Science, American Association for the Advancement of Science, Washington DC, vol. 282, Nov. 1998, pp. 1145-1147.
Thomson, Pluripotent cell lines derived from common marmoset (Callithrix jacchus) blastocysts. (1996), Biol. Reprod., 55:254-259.
Timar et al., Angiogenesis-Dependent Diseases and Angiogenesis Therapy. Pathol Oncol Res. 2001;7(2):85-94.
Tuschl, Effects of cell culture conditions on primary rat hepatocytes-cell morphology and differential gene expression. Toxicology. Feb. 1, 2006;218(2-3):205-15. Epub Dec. 6, 2005.
Valtink et al., Culturing of Retinal Pigment Epithelium Cells, Eye Banking. Dev Ophthalmol. Basel, Karger, 2009, vol. 43, pp. 109-119.
Van Meurs et al., Br J Ophthalmol. Jan. 2004;88(1):110-3. Autologous peripheral retinal pigment epithelium translocation in patients with subfoveal neovascular membranes.
Verfaillie, Stem Cells: Hype and Reality, Hematology Am Soc Hematol Educ Program. 2002:369-81.
Weisz et al., Allogenic fetal retinal pigment epithelial cell transplant in a patient with geographic atrophy, Retina. 1999;19(6):540-5.
Wichterle, Directed differentiation of embryonic stem cells into motor neurons. (2002), Cell, 110:385-397.
Yang, Roles of cell-extrinsic growth factors in vertebrate eye pattern formation and retinogenesis. (2004), Semin Cell Dev Biol., 15:91-103.
Ying et al. "Conversion of Embryonic Stem Cells Into Neuroctodermal Precursors in Adherent Monoculture," Nature Biotechnology, Nature Publishing Group, New York, NY, vol. 21, No. 2, Feb. 2003, pp. 183-186.
Zaghloul et al., "Step-wise specification of retinal stem cells during normal embryogenesis," Biol Cell, May 2005 ;97(5):321-37.
Zeng, Dopaminergic differentiation of human embryonic stem cells. (2004), Stem Cell, 22:925-940.
Zhang et al., "In vitro differentiation of transplantable neural precursors from human embryonic stem cells," Nat Biotechnol., Dec. 2001;19(12):1129-33.
Zhao et al. "Differentiation of Embryonic Stem Cells Into Retinal Neurons," Biochemical and Biophysical Research Communications, vol. 297, No. 2, Sep. 2002, pp. 177-184.
Zhao, Differentiation and transdifferentiation of the retinal pigment epithelium. (1997), International Rev. Cytology, 171:225-266.
Zhao, In vitro transdifferentiation of embryonic rat retinal pigment epithelium to neural retina. (1995), Brain Res., 677:300-310.
Zhou et al. Novel PAX6 binding sites in the human genome and the role of repetitive elements in the evolution of gene regulation. Genome Res. Nov. 2002;12(11):1716-22.
Znoiko, Identification of the RPE65 protein in mammalian cone photoreceptors. (2002), Invest Ophthalmol Vis Sci., 43(5):1604-9.
Aisenbrey et al., Iris pigment epithelial translocation in the treatment of exudative macular degeneration: a 3-year follow-up. Arch Ophthalmol Feb. 2006;124(2):183-8.
Algvere et al., Transplantation of RPE in age-related macular degeneration: observations in disciform lesions and dry RPE atrophy. Graefes Arch Clin Exp Ophthalmol Mar. 1997;235(3):149-58.
Aramant et al., Transplanted sheets of human retina and retinal pigment epithelium develop normally in nude rats. Exp Eye Res. Aug. 2002;75(2):115-25.
Aronson, Human retinal pigment cell culture. In Vitro. Aug. 1983;19(8):642-50.
Berger et al., Photoreceptor transplantation in retinitis pigmentosa: short-term follow-up. Ophthalmology. Feb. 2003;110(2):383-91.
Binder et al., Outcome of transplantation of autologous retinal pigment epithelium in age-related macular degeneration: a prospective trial. Invest Ophthalmol Vis Sci. Nov. 2004;45(11):4151-60.
Binder et al., Transplantation of the RPE in AMD. Prog Retin Eye Res. Sep. 2007;26(5):516-54. Epub Mar. 6, 2007. Abstract Only.
Cai et al., Gene expression profile of cultured adult compared to immortalized human RPE. Mol Vis. Jan. 5, 2006;12:1-14.
Canola et al., Retinal stem cells transplanted into models of late stages of retinitis pigmentosa preferentially adopt a glial or a retinal ganglion cell fate. Invest Ophthalmol Vis Sci. Jan. 2007;48(1):446-54.
Cotsiki et al., Simian virus 40 large T antigen targets the spindle assembly checkpoint protein Bub1. Proc Natl Acad Sci U S A. Jan. 27, 2004;101(4):947-52. Epub Jan. 19, 2004.
Crafoord et al., Experimental transplantation of autologous iris pigment epithelial cells to the subretinal space. Acta Ophthalmol Scand. Oct. 2001;79(5):509-14.
Del Cerro et al., Histologic correlation of human neural retinal transplantation. Invest Ophthalmol Vis Sci. Sep. 2000;41(10):3142-8.
Del Priore et al., Triple immune suppression increases short-term survival of porcine fetal retinal pigment epithelium xenografts. Invest Ophthalmol Vis Sci. Sep. 2003;44(9):4044-53.
Engelmann et al., RPE cell cultivation. Graefes Arch Clin Exp Ophthalmol Jan. 2004;242(1):65-7. Epub Dec. 5, 2003. First Page Only.
Gullapalli et al., Impaired RPE survival on aged submacular human Bruch's membrane. Exp Eye Res. Feb. 2005;80(2):235-48. Abstract Only.
Gupta et al., Mechanism and its regulation of tumor-induced angiogenesis. World J Gastroenterol. Jun. 2003;9(6):1144-55.
Haruta et al., [Regeneration of Retinal Function by Cell Transplantation]. Jikken Igaku, 2002; 20(9):1307-1311.
Hu et al., A cell culture medium that supports the differentiation of human retinal pigment epithelium into functionally polarized monolayers. Molecular Vision. Feb. 7, 2001; 7:14-19 http://www.molvis.org/molvis/v7/a3/ [Last accessed Dec. 4, 2013].
Humayun et al., Human neural retinal transplantation. Invest Ophthalmol Vis Sci. Sep. 2000;41(10):3100-6.
Kohen et al., Mechanisms of graft rejection in the transplantation of retinal pigment epithelial cells. Ophthalmic Res. 1997;29(5):298-304. Abstract only.
Lappas et al., Iris pigment epithelial cell translocation in exudative age-related macular degeneration. A pilot study in patients. Graefes Arch Clin Exp Ophthalmol. Aug. 2000;238(8):631-41. Abstract Only.
Lee et al., Spatial cues for the enhancement of retinal pigment epithelial cell function in potential transplants. Biomaterials. Apr. 2007;28(13):2192-201. Epub Jan. 11, 2007. Abstract only.
Liao et al., Molecular signature of primary retinal pigment epithelium and stem-cell-derived RPE cells. Hum Mol Genet. Nov. 1, 2010;19(21):4229-38. doi: 10.1093/hmg/ddq341. Epub Aug. 13, 2010.

(56) References Cited

OTHER PUBLICATIONS

Little et al., Transplantation of human fetal retinal pigment epithelium rescues photoreceptor cells from degeneration in the Royal College of Surgeons rat retina. Invest Ophthalmol Vis Sci. Jan. 1996;37(1):204-11.

Liu et al., Integrated analysis of DNA methylation and RNA transcriptome during in vitro differentiation of human pluripotent stem cells into retinal pigment epithelial cells. PLoS One. Mar. 17, 2014;9(3):e91416. doi:10.1371/journal.pone.0091416. eCollection 2014.

Lu et al., Expression of melanin-related genes in cultured adult human retinal pigment epithelium and uveal melanoma cells. Mol Vis. Nov. 3, 2007;13:2066-72.

Lu et al., Long-term safety and function of RPE from human embryonic stem cells in preclinical models of macular degeneration. Stem Cells. Sep. 2009;27(9):2126-35. doi: 10.1002/stem.149.

Ma et al., Expression, purification, and MALDI analysis of RPE65. Invest Ophthalmol Vis Sci. Jun. 2001;42(7):1429-35.

Maclaren et al., Autologous transplantation of the retinal pigment epithelium and choroid in the treatment of neovascular age-related macular degeneration. Ophthalmology. Mar. 2007;114(3):561-70. Abstract only.

Maclaren et al., Long-term results of submacular surgery combined with macular translocation of the retinal pigment epithelium in neovascular age-related macular degeneration. Ophthalmology. Dec. 2005;112(12):2081-7. Abstract Only.

Makrides, Components of vectors for gene transfer and expression in mammalian cells. Protein Expr Purif. Nov. 1999;17(2):183-202.

Maminishkis et al., Confluent monolayers of cultured human fetal retinal pigment epithelium exhibit morphology and physiology of native tissue. Invest Ophthalmol Vis Sci. Aug. 2006;47(8):3612-24.

Peyman et al., A technique for retinal pigment epithelium transplantation for age-related macular degeneration secondary to extensive subfoveal scarring. Ophthalmic Surg. Feb. 1991;22(2):102-8.

Proulx et al., Integrin alpha5 expression by the ARPE-19 cell line: comparison with primary RPE cultures and effect of growth medium on the alpha5 gene promoter strength. Exp Eye Res. Aug. 2004;79(2):157-65.

Ray et al., SV40 T antigen alone drives karyotype instability that precedes neoplastic transformation of human diploid fibroblasts. J Cell Biochem. Jan. 1990;42(1):13-31.

Redmond, Focus on Molecules: RPE65, the visual cycle retinol isomerase. Exp Eye Res. May 2009;88(5):846-7. doi: 10.1016/j.exer.2008.07.015. Epub Aug. 14, 2008.

Revazova et al., Patient-specific stem cell lines derived from human parthenogenetic blastocysts. Cloning Stem Cells. 2007 Fall;9(3):432-49.

Sauvé et al., Visual field loss in RCS rats and the effect of RPE cell transplantation. Exp Neurol. Aug. 1998;152(2):243-50. Abstract only.

Schwartz et al., Human embryonic stem cell-derived retinal pigment epithelium in patients with age-related macular degeneration and Stargardt's macular dystrophy: follow-up of two open-label phase 1/2 studies. Lancet. Oct. 15, 2014. pii: S0140-6736(14)61376-3. doi: 10.1016/S0140-6736(14)61376-3. [Epub ahead of print].

Song et al., Propagation of fetal human RPE cells: preservation of original culture morphology after serial passage. J Cell Physiol. Apr. 1990;143(1):196-203. Abstract Only.

Stanga et al., Retinal pigment epithelium translocation after choroidal neovascular membrane removal in age-related macular degeneration. Ophthalmology. Aug. 2002;109(8):1492-8. Abstract only.

Strauss, The retinal pigment epithelium in visual function. Physiol Rev. Jul. 2005;85(3):845-81.

Takahashi, Nihon Saisei-Iryo Gakkai zasshi, 2004; 3(2):76-80.

Tamai, [Retinal pigment epithelial cell transplantation: perspective]. Nihon Ganka Gakkai Zasshi. Dec. 1996;100(12):982-1006.

Tezel et al., Adult retinal pigment epithelial transplantation in exudative age-related macular degeneration. Am J Ophthalmol Apr. 2007;143(4):584-95. Epub Feb. 14, 2007. Abstract Only.

Tezel et al., Serum-free media for culturing and serial-passaging of adult human retinal pigment epithelium. Exp Eye Res. Jun. 1998;66(6):807-15. Abstract Only.

Thumann et al., Transplantation of autologous iris pigment epithelium after removal of choroidal neovascular membranes. Arch Ophthalmol Oct. 2000;118(10):1350-5.

Tian et al., The expression of native and cultured RPE grown on different matrices. Physiol Genomics. Apr. 13, 2004;17(2):170-82. Abstract only.

Tomita et al., Biodegradable polymer composite grafts promote the survival and differentiation of retinal progenitor cells. Stem Cells. Nov.-Dec. 2005;23(10):1579-88.

Treumer et al., Autologous retinal pigment epithelium-choroid sheet transplantation in age related macular degeneration: morphological and functional results. Br J Ophthalmol Mar. 2007;91(3):349-53. Epub Oct. 11, 2006.

Wang et al., Grafting of ARPE-19 and Schwann cells to the subretinal space in RCS rats. Invest Ophthalmol Vis Sci. Jul. 2005;46(7):2552-60.

Zhu et al., Isolation, culture and characteristics of human foetal and adult retinal pigment epithelium. Aust N Z J Ophthalmol May 1998;26 Suppl 1:S50-2.

Fukui et al., ABCA4 gene mutations in Japanese patients with Stargardt disease and retinitis pigmentosa. Invest Ophthalmol Vis Sci. Sep. 2002;43(9):2819-24.

Kaplan et al., Human photoreceptor transplantation in retinitis pigmentosa. A safety study. Arch Ophthalmol Sep. 1997;115(9):1168-72. Abstract only.

Kaplan et al., Retinal transplantation. Chem Immunol. 1999;73:207-19.

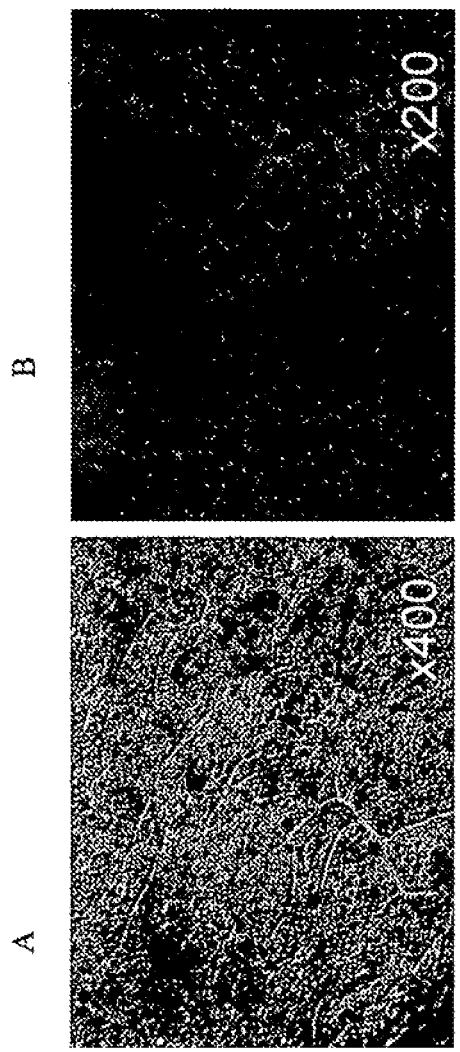

Figure 6A

| Embryonic-RPE | hES-RPE | ARPE-19 | D407 | hES-TD |
|---|---|---|---|---|
| Bestrophin | Bestrophin | - | - | Bestrophin |
| Cathepsin D | Cathepsin D | Cathepsin D | Cathepsin D | Cathepsin D |
| Clusterin-like 1 (retinal) | Clusterin-like 1 (retinal) | - | - | - |
| - | Cellular retinoic acid biding protein 1 | - | - | - |
| Cystatin C | Cystatin C | Cystatin C | Cystatin C | Cystatin C |
| Lens intrinsic membrane protein 2, 19kDA | Lens intrinsic membrane protein 2, 19kDA | | | |
| Lecithin retinol acyltransferase (phosphatidylcholine—retinol O-acyltransferase) | Lecithin retinol acyltransferase (phosphatidylcholine—retinol O-acyltransferase) | | | |
| Microphthalmia-associated transcription factor | Microphthalmia-associated transcription factor | Microphthalmia-associated transcription factor | Microphthalmia-associated transcription factor | Microphthalmia-associated transcription factor |
| NCAM2 | NCAM1 NCAM2 | NCAM1 NCAM2 | - | NCAM1 |
| Ocular development-associated gene | Ocular development-associated gene | Ocular development-associated gene | Ocular development-associated gene | Ocular development-associated gene |
| Oculocutaneous albinism II (pink-eye dilution homolog, mouse) | Oculocutaneous albinism II (pink-eye dilution homolog, mouse) | - | - | - |
| Opsin 3 | Opsin 3 | Opsin 3 PAX4 | Opsin 3 | Opsin 3 |

Figure 6B

| Embryonic-RPE | hES-RPE | ARPE-19 | D407 | hES-TD |
|---|---|---|---|---|
| PAX6 | PAX6 | PAX6 | - | PAX6 |
| PAX8 | PAX8 | PAX8 | PAX8 | PAX8 |
| PEDF | PEDF | - | - | PEDF |
| Phosducin-like | Phosducin | - | - | - |
| - | Prominin 1 | - | - | - |
| Retinal G protein coupled receptor | Retinal G protein coupled receptor | - | - | - |
| Retinal outer segment membrane protein 1 | Retinal outer segment membrane protein 1 | - | Retinal outer segment membrane protein 1 | - |
| - | Retinal pigment epithelium-derived rhodopsin homolog | - | - | Rhodopsin |
| Retinal pigment epithelium-specific protein 65kDa | Retinal pigment epithelium-specific protein 65kDa | - | - | - |
| Retinaldehyde binding protein 1 | Retinaldehyde binding protein 1 | - | - | - |
| Retinol dehydrogenase 5 (11-cis and 9-cis) | Retinol dehydrogenase 5 (11-cis and 9-cis) | - | - | - |
| SOX10 | SOX10 | - | - | - |
| SOX11 | SOX11 | - | - | SOX11 |
| SOX12 | SOX12 | SOX12 | SOX12 | SOX12 |
| - | - | SOX13 | SOX13 | - |
| SOX15 | - | - | SOX15 | - |

Figure 6C

| Embryonic-RPE | hES-RPE | ARPE-19 | D407 | hES-TD |
|---|---|---|---|---|
| SOX17 | SOX17 | - | SOX17 | - |
| SOX4 | SOX4 | SOX4 | SOX4 | SOX4 |
| SOX9 | SOX9 | SOX9 | - | SOX9 |
| Transthyretin | Transthyretin | - | - | - |
| - | Visual system homeobox 1 homolog, CHX10-like (zebrafish) | - | - | Visual system homeobox 1 homolog (CHX10-like (zebrafish) |
| Retriculocalbin 1, EF-hand calcium binding domain | Retriculocalbin 1, EF-hand calcium binding domain | Retriculocalbin 1, EF-hand calcium binding domain | Retriculocalbin 1, EF-hand calcium binding domain | Retriculocalbin 1, EF-hand calcium binding domain |
| Retriculocalbin 2, EF-hand calcium binding domain | Retriculocalbin 2, EF-hand calcium binding domain | Retriculocalbin 2, EF-hand calcium binding domain | Retriculocalbin 2, EF-hand calcium binding domain | Retriculocalbin 2, EF-hand calcium binding domain |
| | | Reticulon 1 | | |
| Reticulon 2 | Reticulon 2 | Reticulon 2 | Reticulon 2 | Reticulon 2 |
| Reticulon 3 | Reticulon 3 | Reticulon 3 | Reticulon 3 | Reticulon 3 |
| Reticulon 4 | Reticulon 4 | Reticulon 4 | Reticulon 4 | Reticulon 4 |
| Retinal short-chain dehydrogenase/reductase 2 | Retinal short-chain dehydrogenase/reductase 2 | Retinal short-chain dehydrogenase/reductase 2 | Retinal short-chain dehydrogenase/reductase 2 | Retinal short-chain dehydrogenase/reductase 2 |
| Retinal short-chain dehydrogenase/reductase 3 | Retinal short-chain dehydrogenase/reductase 3 | Retinal short-chain dehydrogenase/reductase 3 | - | Retinal short-chain dehydrogenase/reductase 3 |

Figure 6D

| Embryonic-RPE | hES-RPE | ARPE-19 | D407 | hES-TD |
|---|---|---|---|---|
| Retinal short-chain dehydrogenase/reductase 4 | Retinal short-chain dehydrogenase/reductase 4 | Retinal short-chain dehydrogenase/reductase 4 | Retinal short-chain dehydrogenase/reductase 4 | Retinal short-chain dehydrogenase/reductase 4 |
| Retinitis pigmentosa 2 (X-linked recessive) | Retinitis pigmentosa 2 (X-linked recessive) | Retinitis pigmentosa 2 (X-linked recessive) | Retinitis pigmentosa 2 (X-linked recessive) | Retinitis pigmentosa 2 (X-linked recessive) |
| Retinitis pigmentosa GTPase regulator | Retinitis pigmentosa GTPase regulator | Retinitis pigmentosa GTPase regulator | Retinitis pigmentosa GTPase | - |
|  |  | Retinitis pigmentosa GTPase regulator interacting protein 1 | Regulator interacting protein 1 | - |
| Retinoblastoma 1 (including osteosarcoma) | Retinoblastoma 1 (including osteosarcoma) | Retinoblastoma 1 (including osteosarcoma) | Retinoblastoma 1 (including osteosarcoma) | Retinoblastoma 1 (including osteosarcoma) |
|  |  | Retinoblastoma-like 1 (p107) | Retinoblastoma-like 1 (p107) | - |
| Retinoblastoma binding protein 1 | Retinoblastoma binding protein 1 | Retinol binding protein 1, cellular | Retinol binding protein 1 | Retinol binding protein 1, cellular |
| Retinoblastoma binding protein 1-like 1 | Retinoblastoma binding protein 1-like 1 | Retinoblastoma binding protein 1-like 1 | Retinoblastoma binding protein 1-like 1 | Retinoblastoma binding protein 1-like 1 |
| Retinoblastoma binding protein 2 | Retinoblastoma binding protein 2 | Retinoblastoma binding protein 2 | Retinoblastoma binding protein 2 | Retinoblastoma binding protein 2 |
| Retinoblastoma binding protein 4 | Retinoblastoma binding protein 4 | Retinoblastoma binding protein 4 | Retinoblastoma binding protein 4 | Retinoblastoma binding protein 4 |
| Retinoblastoma binding protein 5 | - | Retinoblastoma binding protein 5 |  |  |

Figure 6E

| Embryonic-RPE | hES-RPE | ARPE-19 | D407 | hES-TD |
|---|---|---|---|---|
| Retinoblastoma binding protein 6 | Retinoblastoma binding protein 6 | Retinoblastoma binding protein 6 | Retinoblastoma binding protein 5 | |
| Retinoblastoma binding protein 7 | Retinoblastoma binding protein 7 | Retinoblastoma binding protein 7 | Retinoblastoma binding protein 6 | Retinoblastoma binding protein 6 |
| Retinoblastoma binding protein 8 | Retinoblastoma binding protein 8 | Retinoblastoma binding protein 8 | Retinoblastoma binding protein 7 | Retinoblastoma binding protein 7 |
| - | Retinoblastoma binding protein 9 | - | Retinoblastoma binding protein 8 | Retinoblastoma binding protein 8 |
| Retinoblastoma-associated factor 600 | Retinoblastoma-associated factor 600 | Retinoblastoma-associated factor 600 | | Retinoblastoma binding protein 9 |
| Retinoblastoma-associated protein 140 | Retinoblastoma-associated protein 140 | Retinoblastoma-associated protein 140 | Retinoblastoma-associated factor 600 | Retinoblastoma-associated factor 600 |
| Retinoblastoma-like 2 (p130) | Retinoblastoma-like 2 (p130) | Retinoblastoma-like 2 (p130) | Retinoblastoma-associated protein 140 | Retinoblastoma-associated protein 140 |
| | - | Retinoic acid- and interferono-inducible protein (58kD) | Retinoblastoma-like 2 (p130) | Retinoblastoma-like 2 (p130) |
| | Retinoic acid induced 1 | - | Retinoic acid- and interferono-inducible protein (58kD) | - |
| | - | Retinoic acid induced 3 | - | Retinoic acid induced 1 |
| Retinoic acid induced 14 | Retinoic acid induced 14 | Retinoic acid induced 14 | Retinoic acid induced 3 | Retinoic acid induced 3 |
| Retinoic acid induced 16 | Retinoic acid induced 16 | Retinoic acid induced 16 | Retinoic acid induced 14 | Retinoic acid induced 14 |
| Retinoic acid induced 17 | Retinoic acid induced 17 | Retinoic acid induced 17 | Retinoic acid induced 16 | Retinoic acid induced 16 |

Figure 6F

| Embryonic-RPE | hES-RPE | ARPE-19 | D407 | hES-TD |
|---|---|---|---|---|
| Retinoic acid receptor responder (tazarotene induced) 2 | Retinoic acid induced 2 | - | Retinoic acid induced 17 | Retinoic acid induced 17 |
| - | Retinoic acid receptor responder (tazarotene induced) 3 | Retinoic acid receptor responder (tazarotene induced) 3 | Retinoic acid receptor responder (tazarotene induced) 3 | - |
| - | Retinoic acid receptor, beta | - | Retinoic acid receptor, alpha | Retinoic acid receptor, alpha |
| Retinoic acid receptor, beta | Retinoic acid receptor, alpha | - | Retinoic acid receptor, beta | Retinoic acid receptor, beta |
| - | Retinoic acid repressible protein | Retinoic acid repressible protein | Retinoic acid repressible protein | Retinoic acid repressible protein |
| Retinoic acid repressible protein | Retinoid X receptor, alpha | Retinoid X receptor, alpha | Retinoid X receptor, alpha | Retinoid X receptor, alpha |
| Retinoid X receptor, alpha | Retinoid X receptor, beta | Retinoid X receptor, beta | Retinoid X receptor, beta | Retinoid X receptor, beta |
| Retinoid X receptor, beta | Retinol binding protein 1, cellular | - | - | Retinol binding protein 1, cellular |
| Retinol binding protein 1, cellular | Retinol dehydrogenase 11 (all-trans and 9-cis) | Retinol dehydrogenase 11 (all-trans and 9-cis) | Retinol dehydrogenase 11 (all-trans and 9-cis) | Retinol dehydrogenase 11 (all-trans and 9-cis) |
| Retinol dehydrogenase 11 (all-trans and 9-cis) | Retinol dehydrogenase 14 (all-trans and 9-cis) | Retinol dehydrogenase 14 (all-trans and 9-cis) | Retinol dehydrogenase 14 (all-trans and 9-cis) | Retinol dehydrogenase 14 (all-trans and 9-cis) |
| Retinol dehydrogenase 14 (all-trans and 9-cis) | | | | Retinoschisis (X-linked, juvenile) 1 |

Figure 6G

| Melanin biosynthesis | Retinitis pigmentosa | Vision | Retinol-binding |
|---|---|---|---|
| Dopachrome tautomerase (dopachrome delta-isomerase, tyrosine-related protein 2) | Retinal outer segment membrane protein 1 | Retinal outer segment membrane protein 1 | Retinal outer segment membrane protein 1 |
| Dopachrome tautomerase (dopachrome delta-isomerase, tyrosine-related protein 2) | c-mer proto-oncogene tyrosine kinase | c-mer proto-oncogene tyrosine kinase | Transthyretin (prealbumin, amyloidosis type I) |
| Tyrosinase (oculocutaneous albinism 1A) | Retinaldehyde binding protein 1 | Retinaldehyde binding protein 1 | |
| Silver homolog (mouse) | Retinal G protein coupled receptor | Retinal G protein coupled receptor | |
| Membrane associated transporter | Retinal pigment epithelium-specific protein 65kDa | Retinal pigment epithelium-specific protein 65kDa | |
| Membrane associated transporter | | Vitelliform macular dystrophy (Best disease, bestrophin) | |
| | | Retinol dehydrogenase 5 (11-cis and 9-cis) | |
| | | Membrane associated transporter | |

MODALITIES FOR THE TREATMENT OF DEGENERATIVE DISEASES OF THE RETINA

RELATED APPLICATIONS

This application is a continuation of U.S. application Ser. No. 13/477,763, filed May 22, 2012, which is a continuation of U.S. application Ser. No. 12/857,911, filed Aug. 17, 2010 (now U.S. Pat. No. 8,268,303), which is a continuation of U.S. application Ser. No. 11/041,382, filed Jan. 24, 2005 (now U.S. Pat. No. 7,794,704), which claims the benefit of U.S. Provisional Application No. 60/538,964, filed Jan. 23, 2004, each of which is hereby incorporated by reference herein in its entirety.

FIELD OF THE INVENTION

This invention relates generally to methods for improved cell-based therapies for retinal degeneration and other visual disorders as well as treatment of Parkinson's disease and for differentiating mammalian embryonic stem cells and mammalian embryo-derived cells into retinal pigment epithelium (RPE) cells and other eye tissue including, but not limited to) rods, cones, bipolar, corneal, neural, iris epithelium, and progenitor cells.

BACKGROUND OF THE INVENTION

Many parts of the central nervous system (CNS) exhibit laminar organization, and neuropathological processes generally involve more than one of these multiple cellular layers. Diseases of the CNS frequently include neuronal cell loss, and, because of the absence of endogenous repopulation, effective recovery of function following CNS-related disease is either extremely limited or absent. In particular, the common retinal condition known as age-related macular degeneration (AMD) results from the loss of photoreceptors together with the retinal pigment epithelium (RPE), with additional variable involvement of internuncial ("relay") neurons of the inner nuclear layer (INL). Restoration of moderate-to-high acuity vision, therefore, requires the functional replacement of some or all of the damaged cellular layers.

Anatomically, retinitis pigmentosa (RP), a family of inherited retinal degenerations, is a continuing decrease in the number of photocreceptor cell nuclei which leads to loss of vision. Although the phenotype is similar across most forms of RP, the underlying cellular mechanisms are diverse and can result from various mutations in many genes. Most involve mutations that alter the expression of photoreceptor-cell-Specific genes, with mutations in the rhodopsin gene accounting for approximately 10% of these. In other forms of the disease, the regulatory genes of apoptosis are altered (for example, Bax and Pax2). AMD is a clinical diagnosis encompassing a range of degenerative conditions that likely differ in etiology at the molecular level. All cases of AMD share the feature of photoreceptor cell loss within the central retina. However, this common endpoint appears to be a secondary consequence of earlier abnormalities at the level of the RPE, neovascularization, and underlying Bruch's membrane. The latter may relate to difficulties with photoreceptor membrane turnover, which are as yet poorly understood. Additionally, the retinal pigment epithelium is one of the most important cell types in the eye, as it is crucial to the support of the photoreceptor function. It performs several complex tasks, including phagocytosis of shed outer segments of rods and cones, vitamin A metabolism, synthesis of mucoploysacharides involved in the metabolite exchange in the subretinal space, transport of metabolites, regulation of angiogenesis, absorption of light, enhancement of resolution of images, and the regulation of many other functions in the retina through secreted proteins such as proteases and protease inhibitors.

An additional feature present in some cases of AMD is the presence of aberrant blood vessels, which result in a condition known as choroidal neovascularization (CNV). This neovascular ("wet") form of AMD is particularly destructive and seems to result from a loss of proper regulation of angiogenesis. Breaks in Bruch's membrane as a result of RPE dysfunction allows new vessels from the choroidal circulation access to the subretinal space, where they can physically disrupt outer-segment organization and cause vascular leakage or hemorrhage leading to additional photoreceptor loss.

CNV can be targeted by laser treatment. Thus, laser treatment for the "wet" form of AMD is in general use in the United States. There are often undesirable side effects, however, and therefore patient dissatisfaction with treatment outcome. This is due to the fact that laser burns, if they occur, are associated with photoreceptor death and with absolute, irreparable blindness within the corresponding part of the visual field. In addition, laser treatment does not fix the underlying predisposition towards developing CNV. Indeed, laser burns have been used as a convenient method for induction of CNV in monkeys (Archer and Gardiner, 1981). Macular laser treatments for CNV are used much more sparingly in other countries such as the U.K. There is no generally recognized treatment for the more common "dry" form of AMD, in which there is photoreceptor loss overlying irregular patches of RPE atrophy in the macula and associated extracellular material called drusen.

Since RPE plays an important role in photoreceptor maintenance, and regulation of angiogenesis, various RPE malfunctions in vivo are associated with vision-altering ailments, such as retinitis pigmentosa, RPE detachment, displasia, athrophy, retinopathy, macular dystrophy or degeneration, including age-related macular degeneration, which can result in photoreceptor damage and blindness. Specifically and in addition to AMD, the variety of other degenerative conditions affecting the macula include, but are not limited to, cone dystrophy, cone-rod dystrophy, malattia leventinese, Doyne honeycomb dystrophy, Sorsby's dystrophy, Stargardt disease, pattern/butterfly dystrophies, Best vitelliform dystrophy, North Carolina dystrophy, central areolar choroidal dystrophy, angioid streaks, and toxic maculopathies.

General retinal diseases that can secondarily effect the macula include retinal detachment, pathologic myopia, retinitis pigmentosa, diabetic retinopathy, CMV retinitis, occlusive retinal vascular disease, retinopathy of prematurity (ROP), choroidal rupture, ocular histoplasmosis syndrome (POHS), toxoplasmosis, and Leber's congenital amaurosis. None of the above lists is exhaustive.

All of the above conditions involve loss of photoreceptors and, therefore, treatment options are few and insufficient.

Because of its wound healing abilities, RPE has been extensively studied in application to transplantation therapy. In 2002, one year into the trial, patients were showing a 30-50% improvement. It has been shown in several animal models and in humans (Gouras et al., 2002, Stanga et al., 2002, Binder et al., 2002, Schraermeyer et al., 2001, reviewed by Lund et al., 2001) that RPE transplantation has a good potential of vision restoration. However, even in an immune-privileged site such as the eye, there is a problem with graft rejection, hindering the progress of this approach if allogenic transplantation is used. Although new photoreceptors (PRCs) have been introduced experimentally by transplantation, grafted PRCs show a marked reluctance to link up with surviving neurons of the host retina. Reliance on RPE cells derived from fetal tissue is another problem, as these cells have shown a very low proliferative potential. Emory University researchers performed a trial where they cultured RPE cells from a human eye donor in vitro and transplanted them into six patients with advanced Parkinson's Disease. Although a 30-50% decrease in symptoms was found one year after transplantation, there is a shortage of eye donors, this is not yet FDA approved, and there would still exist a need beyond what could be met by donated eye tissue.

Thus far, therapies using ectopic RPE cells have been shown to behave like fibroblasts and have been associated with a number of destructive retinal complications including axonal loss (Villegas-Perez, et al, 1998) and proliferative vitreoretinopathy (PVR) with retinal detachment (Cleary and Ryan, 1979). RPE delivered as a loose sheet tends to scroll up. This results in poor effective coverage of photoreceptors as well as a multilayered RPE with incorrect polarity, possibly resulting in cyst formation or macular edema.

Delivery of neural retinal grafts to the subretinal (submacular) space of the diseased human eye has been described in Kaplan et al. (1997), Humayun et al. (2000), and del Cerro et al. (2000). A serious problem exists in that the neural retinal grafts typically do not functionally integrate with the host retina. In addition, the absence of an intact RPE monolayer means that RPE dysfunction or disruption of Bruch's membrane has not been rectified. Both are fundamental antecedents of visual loss.

Thus, there exists no effective means for reconstituting RPE in any of the current therapies and there remain deficiencies in each, particularly the essential problem of a functional disconnection between the graft and the host retina. Therefore there exists the need for an improved retinal therapy.

SUMMARY OF THE INVENTION

The purpose of the present invention is to provide improved methods for the derivation of eye cells including, but not limited to, neural cells, including horizontal cells and amacrine cells, retinal cells such as rods and cones, corneal cells, vascular cells, and RPE and RPE-like cells from stem cells and to provide improved methods and therapies for the treatment of retinal degeneration. In particular, these methods involve the use of RPE and RPE-like cells derived from human embryonic stem cells.

One embodiment of the present invention provides an improved method of generating cells for therapy for retinal degeneration using RPE cells, RPE-like cells, the progenitors of these cells or a combination of two or three of any of the preceding derived from mammalian embryonic stem cells in order to treat various conditions including but not limited to retinitis pigmentosa and macular degeneration and associated conditions. The cell types which can be produced using this invention include, but are not limited to, RPE, RPE-like cells, and RPE progenitors. Cells which may also be produced include iris pigmented epithelial (IPE) cells. Vision associated neural cells including internuncial neurons (e.g. "relay" neurons of the inner nuclear layer (INL)) and amacrine cells (interneurons that interact at the second synaptic level of the vertically direct pathways consisting of the photoreceptor-bipolar-ganglion cell chain—they are synaptically active in the inner plexiform layer (IPL) and serve to integrate, modulate and interpose a temporal domain to the visual message presented to the ganglion cell) can also be produced using this invention. Additionally, retinal cells, rods, cones, and corneal cells can be produced. In a further embodiment of the present invention, cells providing the vasculature of the eye can also be produced. The cells of the present invention may be transplanted into the subretinal space by using vitrectomy surgery. Non-limiting examples include the transplantation of these cells in a suspension, matrix, or substrate. Animal models of retinitis pigmentosa that may be treated include rodents (rd mouse, RPE-65 knockout mouse, tubby-like mouse, RCS rat, cats (Abyssinian cat), and dogs (cone degeneration "cd" dog, progressive rod-cone degeneration "prcd" dog, early retinal degeneration "erd" dog, rod-cone dysplasia 1, 2 & 3 "rcd1, rcd2 & rcd3" dogs, photoreceptor dysplasia "pd" dog, and Briard "RPE-65" (dog). Evaluation is performed using behavioral tests, fluorescent angiography, histology, or functional testing such as measuring the ability of the cells to perform phagocytosis (photoreceptor fragments), vitamin A metabolism, tight junctions conductivity, or evaluation using electron microscopy. One of the many advantages to the methods presented here is the ability to produce and treat many more patients than it would be possible to treat if one were limited to using eye donor tissue.

A further embodiment of the present invention provides methods for the spontaneous differentiation of hES cells into cells with numerous characteristics of RPE. These RPE preparations are capable of phenotypic changes in culture and maintaining RPE characteristics through multiple passages. The present invention also provides for methods of differentiation of established RPE cell lines into alternate neuronal lineages, corneal cells, retinal cells as a non-limiting example through the use of bFGF or FGF.

Another embodiment of the present invention is a method for the derivation of new RPE lines and progenitor cells from existing and new ES cell lines. There can be variations in the properties, such as growth rate, expression of pigment, or dedifferentiation and re-differentiation in culture, of RPE-like cells when they are derived from different ES cell lines. There can be certain variations in their functionality and karyotypic stability, so it is desirable to provide methods for the derivation of new RPE lines and new ES cell lines which would allow choosing the lines with desired properties that can be clonally selected to produce a pure population of high quality RPE-like cells.

Cells which may also be derived from existing and new ES cell lines include iris pigmented epithelial (IPE) cells. In an additional embodiment, vision associated neural cells including internuncial neurons (e.g. "relay" neurons of the inner nuclear layer (INL)) and amacrine cells can also be produced using this invention. Additionally, retinal cells, rods, cones, and corneal cells can be produced. In a further embodiment of the present invention, cells providing the vasculature of the eye can also be produced.

Another embodiment of the present invention is a method for the derivation of RPE lines or precursors to RPE cells that have an increased ability to prevent neovascularization. Such cells can be produced by aging a somatic cell from a patient such that telomerase is shortened where at least 10% of the normal replicative lifespan of the cell has been passed, then the use of said somatic cell as a nuclear transfer donor cell to create cells that overexpress angiogenesis inhibitors such as Pigment Epithelium Derived Factor (PEDF/EPC-1). Alternatively such cells may be genetically modified with exogenous genes that inhibit neovascularization.

Another embodiment of the present invention utilized a bank of ES or embryo-derived cells with homozygosity in the HLA region such that said cells have reduced complexity of their HLA antigens.

Therefore, an additional embodiment of the present invention includes the characterization of ES-derived RPE-like cells. Although the ES-derived pigmented epithelial cells strongly resemble RPE by their morphology, behavior and molecular markers, their therapeutic value will depend on their ability to perform RPE functions and to remain non-carcinogenic. Therefore, the ES-derived RPE cells are characterized using one or more of the following techniques: (i) assessment of their functionality, i.e. phagocytosis of the photoreceptor fragments, vitamin A metabolism, wound healing potential; (ii) evaluation of the pluripotency of RPE-like ES cells derivatives through animal model transplantations, (as a non-limiting example this can include SCID mice); (iii) phenotyping and karyotyping of RPE-like cells; (iv) evaluation of ES cells-derived RPE-like cells and RPE tissue by gene expression profiling, (v) evaluation of the expression of molecular markers of RPE at the protein level, including bestrophin, CRALBP, RPE-65, PEDF. The cells can also be evaluated based on their expression of transcriptional activators normally required for the eye development, including rx/rax, chx10/vsx-2/alx, ots-1, otx-2, six3/optx, six6/optx2, mitf, pax6/mitf, and pax6/pax2 (Fischer and Reh, 2001, Baumer et al., 2003).

An additional embodiment of the present invention is a method for the characterization of ES-derived RPE-like cells using at least one of the techniques selected from the group consisting of (i) assessment of the ES-derived RPE-like cells functionality; (ii) evaluation of the pluripotency of RPE-like ES cell derivatives through animal model transplantations; (iii) phenotyping and karyotyping of RPE-like cells; (iv) evaluation of gene expression profiling, (v) evaluation of the expression of molecular markers of RPE at the protein level; and (vi) the expression of transcriptional activators normally required for the eye development. In a further embodiment these techniques may be used for the assessment of multiple hES cell-derived cell types.

Another embodiment of the present invention is a method for the derivation of RPE cells and RPE precursor cells directly from human and non-human animal morula or blastocyst-staged embryos (EDCs) without the generation of ES cell lines.

Embryonic stem cells (ES) can be indefinitely maintained in vitro in an undifferentiated state and yet are capable of differentiating into virtually any cell type. Thus human embryonic stem (hES) cells are useful for studies on the differentiation of human cells and can be considered as a potential source for transplantation therapies. To date, the differentiation of human and mouse ES cells into numerous cell types have been reported (reviewed by Smith, 2001) including cardiomyocytes [Kehat et al. 2001, Mummery et al., 2003 Carpenter et al., 2002], neurons and neural precursors (Reubinoff et al. 2000, Carpenter et al. 2001, Schuldiner et al., 2001), adipocytes (Bost et al., 2002, Aubert et al., 1999), hepatocyte-like cells (Rambhatla et al., 2003), hematopoetic cells (Chadwick et al., 2003). oocytes (Hubner et al., 2003), thymocyte-like cells (Lin R Y et al., 2003), pancreatic islet cells (Kahan, 2003), and osteoblasts (Zur Nieden et al., 2003). Another embodiment of the present invention is a method of identifying cells such as RPE cells, hematopoietic cells, muscle cells, liver cells, pancreatic beta cells, neurons, endothelium, progenitor cells or other cells useful in cell therapy or research, derived from embryos, embryonic stem cell lines, or other embryonic cells with the capacity to differentiate into useful cell types by comparing the messenger RNA transcripts of such cells with cells derived in-vivo. This method facilitates the identification of cells with a normal phenotype and for deriving cells optimized for cell therapy for research.

The present invention provides for the differentiation of human ES cells into a specialized cell in the neuronal lineage, the retinal pigment epithelium (RPE). RPE is a densely pigmented epithelial monolayer between the choroid and neural retina. It serves as a part of a barrier between the bloodstream and retina, and it's functions include phagocytosis of shed rod and cone outer segments, absorption of stray light, vitamin A metabolism, regeneration of retinoids, and tissue repair. (Grierson et al., 1994, Fisher and Reh, 2001, Marmorstein et al., 1998). The RPE is easily recognized by its cobblestone cellular morphology of black pigmented cells. In addition, there are several known markers of the RPE, including cellular retinaldehyde-binding protein (CRALBP), a cytoplasic protein that is also found in apical microvilli (Bunt-Milam and Saari, 1983); RPE65, a cytoplasmic protein involved in retinoid metabolism (Ma et al., 2001, Redmond et al., 1998); bestrophin, the product of the Best vitelliform macular dystrophy gene (VMD2, Marmorstein et al., 2000), and pigment epithelium derived factor (PEDF) a 48 kD secreted protein with angiostatic properties (Karakousis et al., 2001, Jablonski et al., 2000).

An unusual feature of the RPE is its apparent plasticity. RPE cells are normally mitotically quiescent, but can begin to divide in response to injury or photocoagtilation. RPE cells adjacent to the injury flatten and proliferate forming a new monolayer (Zhao et al, 1997). Several studies have indicated that the RPE monolayer can produce cells of fibroblast appearance that can later revert to their original RPE morphology (Grierson et al., 1994, Kirchhof et al., 1988, Lee et al., 2001). It is unclear whether the dividing cells and pigmented epithelial layer are from the same lineage as two populations of RPE cells have been isolated: epithelial and fusiforms. (McKay and Burke, 1994). In vitro, depending on the combination of growth factors and substratum, RPE can be maintained as an epithelium or rapidly dedifferentiate and become proliferative (Zhao 1997, Opas and Dziak, 1994). Interestingly, the epithelial phenotype can be reestablished in long-term quiescent cultures (Griersion et al., 1994).

In mammalian development, RPE shares the same progenitor with neural retina, the neuroepithelium of the optic vesicle. Under certain conditions, it has been suggested that RPE can transdifferentiate into neuronal progenitors (Opas and Dziak, 1994), neurons (Chen et al., 2003, Vinores et al., 1995), and lens epithelium (Eguchi, 1986). One of the factors which can stimulate the change of RPE into neurons is bFGF (Opaz and Dziak, 1994, a process associated with the expression of transcriptional activators normally required for the eye development, including rx/rax, chx10/vsx-2/alx, ots-1, otx-2, six3/optx, six6/optx2, mitf, and pax6/pax2 (Fischer and Reh, 2001, Baumer et al., 2003). Recently, it has been shown that the margins of the chick retina contain neural stem cells (Fischer and Reh, 2000) and that the pigmented cells in that area, which express pax6/mitf, can form neuronal cells in response to FGF (Fisher and Reh, 2001).

The present invention provides for the derivation of trabecular meshwork cells from hES and also for genetically modified trabecular meshwork cells for the treatment of glaucoma.

The present invention also provides for the derivation of trabecular meshwork cells from RPE progenitors and RPE-like cells and also for genetically modified trabecular meshwork cells for the treatment of glaucoma.

The present invention includes methods for the derivation of RPE cells and RPE precursor cells directly from human and non-human animal morula or blastocyst-staged embryos (EDCs) without the generation of ES cell lines, comprising a) maintaining ES cells in vitro in an undifferentiated state; b) differentiating the ES cells into RPE and RPE precursor cells;

and, c) identifying cells the RPE cells by comparing the messenger RNA transcripts of such cells with cells derived in-vivo.

Further provided by the present invention are methods for the derivation of RPE lines or precursors to RPE cells that have an increased ability to prevent neovascularization, said methods comprising: a) aging a somatic cell from an animal such that telomerase is shortened wherein at least 10% of the normal replicative lifespan of the cell has been passed; and, b) using the somatic cell as a nuclear transfer donor cell to create cells that overexpress angiogenesis inhibitors, wherein the angiogenesis inhibitors can be Pigment Epithelium Derived Factor (PEDF/EPC-1).

The present invention provides methods for the treatment of Parkinson's disease with hES cell-derived RPE, RPE-like and/or RPE progenitor cells. These may be delivered by stereotaxic intrastriatal implantation with or microcarriers. Alternately, they may be delivered without the use of microcarriers. The cells may also be expanded in culture and used in the treatment of Parkinson's disase by any method known to those skilled in the art.

Other features and advantages of the invention will be apparent from the following detailed description.

BRIEF DESCRIPTION OF THE DRAWINGS

FIG. 1A is a photograph of pigmented regions in a 2.5 month old adherent culture, a well of a 6-well plate, scanned; FIG. 1B is a photograph of pigmented regions in a 2.5 month old cultured grown in EB, at 45× magnification; FIG. 1C is a photograph of a pigmented area of an adherent culture; FIG. 1D is a photograph of a pigmented region of an EB grown culture; FIG. 1E is a photograph of the boundary between pigmented region and the rest of the culture, ×200; FIG. F same as FIG. E but at ×400 magnification. Arrows in A and B point to pigmented regions FIG. 2A-F. is a series of photographs which show the loss and regain of pigmentation and epithelial morphology in culture.

FIGS. 3A and 3B are photographs showing immunolocalization of RPE marker, bestrophin and corresponding phase microscopy field, ×200 magnification; FIGS. 3C and 3D are photographs showing CRALBP and corresponding phase contrast microscopy field, ×400 magnification. Arrows show the colocalization of bestrophin (A) and CRALBP (C) to pigmented cells (C,D); arrowheads point to the absence of staining for these proteins (A,B) in non-pigmented regions (C,D)

FIG. 3, Right Panel shows a photograph and graph of western blot of cell lysates (line hES #36) with antibodies to bestrophin (a) and CRALBP (b); c,d-undifferentiated hES cells, c-control to anti-CRALBP antibody, d-control to anti-bestrophin antibody FIG. 4C, FIG. 4G—phase contrast, FIG. 4D, FIG. 4H—merged images of Pax6/mitf/phase contrast (FIG. 4A, FIG. 4B, FIG. 4C) and Pax2/mitf/phase contrast (FIG. 4E, FIG. 4F, FIG. 4G).

FIG. 5A-B show photographs of RPE differentiation in the culture of human embryo-derived cells: bypassing the stage of derivation of ES cell lines.

FIG. 6 shows the transcriptional comparison of RPE preparations. FIG. 6A-F—Based on the Ontological annotation, this table represents the expression patterns of RPE related genes for hES cell-derived retinal pigment epithelium (hES-RPE), hES cell derived transdifferentiated (hES-RPE-TD), ARPE-19 and D407, and freshly isolated human RPE (fe-RPE). FIG. 6G—Further data mining revealed known RPE specific ontologies, such as melanin biosynthesis, vision, retinol-binding, only in fetal RPE and ES-RPE but not ARPE-19.

DETAILED DESCRIPTION OF THE INVENTION

Figure 1:
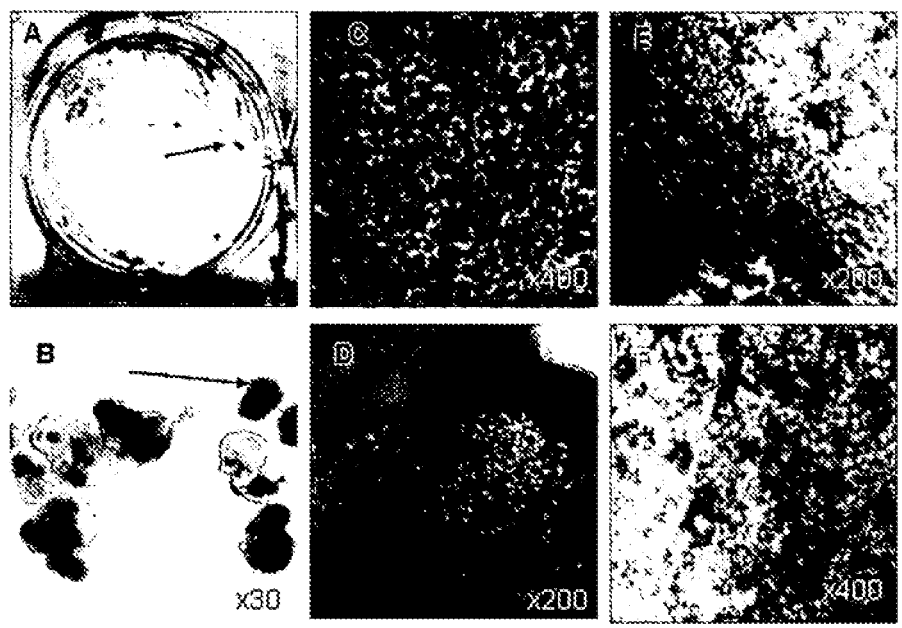
FIG. 1A-F. is a series of photographs showing the appearance of pigmented areas (characteristic of RPE cells) in spontaneously differentiating hES cells.

Various embodiments of the invention are described in detail and may be further illustrated by the provided examples. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The terms used in this specification generally have their ordinary meanings in art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and scope of the invention so long as data are processed, sampled, converted, or the like according to the invention without regard for any particular theory or scheme of action.

Definitions

By "embryo" or "embryonic" is meant a developing cell mass that has not implanted into the uterine membrane of a maternal host. An "embryonic cell" is a cell isolated from or contained in an embryo. This also includes blastomeres, obtained as early as the two-cell stage, and aggregated blastomeres.

The term "embryonic stem cells" refers to embryo-derived cells. More specifically it refers to cells isolated from the inner cell mass of blastocysts or morulae and that have been serially passaged as cell lines.

The term "human embryonic stem cells" (hES cells) refers human embryo-derived cells. More specifically hES refers to cells isolated from the inner cell mass of human blastocysts or morulae and that have been serially passaged as cell lines and can also include blastomeres and aggregated blastomeres.

The term "human embryo-derived cells" (hEDC) refers to morula-derived cells, blastocyst-derived cells including those of the inner cell mass, embryonic shield; or epiblast, or other totipotent or pluripotent stem cells of the early embryo, including primitive endoderm, ectoderm, and mesoderm and their derivatives, also including blastomeres and cell masses from aggregated single blastomeres or embryos from varying stages of development, but excluding human embryonic stem cells that have been passaged as cell lines.

Embryonic stem (ES) cells which have the ability to differentiate into virtually any tissue of a human body can provide a limitless supply of rejuvenated and histocompatible cells for transplantation therapy, as the problem of immune rejection can be overcome with nuclear transfer and parthenogenetic technology. The recent findings of Hirano et al (2003) have shown that mouse ES cells can produce eye-like structures in differentiation experiments in vitro. Among those, pigmented epithelial cells were described, resembling retinal pigment epithelium.

Preliminary experiments carried out at Advanced Cell Technology with primate and human ES cell lines show that a in a specialized culture system these cells differentiate into RPE-like cells that can be isolated and passaged. Human and mouse NT, Cyno parthenote ES cell derivatives have multiple features of RPE: these pigmented epithelial cells express four molecular markers of RPE—bestrophin, CRALBP, PEDF, and RPE65; like RPE, their proliferation in culture is accompanied by dedifferentiation—loss of pigment and epithelial morphology, both of which are restored after the cells form a monolayer and become quiescent. Such RPE-like cells can be easily passaged, frozen and thawed, thus allowing their expansion.

The inventors have further shown that human ES cells also produce multiple eye (vitreous body)-like structures in differentiation experiments in vitro. Histological analysis of these structures show a pattern of cells consistent with early retinal development, including aggregates of cells similar to rods and cones.

RPE Transplantation

At present, chronic, slow rejection of the RPE allografts prevents scientists from determining the therapeutic efficacy of this RPE transplantation. Several methods are being considered to overcome this obstacle. The easiest way is to use sykemic immunosuppression, which is associated with serious side-effects such as cancer and infection. A second approach is to transplant the patient's own RPE, i.e. homografts, but this has the drawback of using old, diseased RPE to replace even more diseased RPE. Yet, a third approach is to use iris epithelium (IPE) from the same patient but this has the drawback that IPE may not perform all the vision related functions of RPE. Ultimately a method will need to be found to eliminate rejection and then scientists can determine the true efficacy of RPE transplantation in AMD and ARMD. Nuclear transfer and parthenogenesis facilitate histocompatibility of grated RPE cells and progenitors.

RPE Defects in Retinitis Pigmentosa

Retinitis pigmentosa is a hereditary condition in which the vision receptors are gradually destroyed through abnormal genetic programming. Some forms cause total blindness at relatively young ages, where other forms demonstrate characteristic "bone spicule" retinal changes with little vision destruction. This disease affects some 1.5 million people worldwide. Two gene defects that cause autosomal recessive RP have been found in genes expressed exclusively in RPE: one is due to an RPE protein involved in vitamin A metabolism (cis retinaldehyde binding protein), a second involves another protein unique to RPE, RPE65. Once rejection is conquered, both of these forms of RP should be treatable immediately by RPE transplantation. This treatment was inconceivable a few years ago when RP was a hopelessly untreatable and a poorly understood form of blindness.

New research in RPE transplantation suggests there is promise for the treatment of retinal degeneration, including macular degeneration. In addition, a number of patients with advanced RP have regained some useful vision following fetal retinal cell transplant. One of the patients, for instance, improved from barely seeing light to being able to count fingers held at a distance of about six feet from the patient's face. In a second case, vision improved to ability to see letters through tunnel vision. The transplants in these studies were performed by injection, introducing the new retinal cells underneath the existing neural retina. Not all of the cells survived since the transplanted fetal cells were allogeneic (i.e. not genetically-matched), although those that did survive formed connections with other neurons and begin to function like the photoreceptors around them. Approximately a year after the first eight people received the transplants, four have recovered some visual function and a fifth shows signs of doing so.

Three newly derived human embryonic stem cell lines are similar in properties to those described earlier (Thomson et al. 1998, Reibunoff et al., 2000, Richards et al., 2000, Lanzendorf et al., 2001): they maintain undifferentiated phenotype and express known markers of undifferentiated hES cells, Oct-4, alkaline phosphatase, SSEA-3, SSEA-4, TRA-I-60, TRA-I-81 through 45 passages in culture or over 130 population doublings. All hES cell lines differentiate into derivatives of three germ layers in EB or long term adherent cultures and in teratomas. One of the differentiation derivatives of hES cells is similar to retinal pigment epithelium by the following criteria: morphologically, they have a typical epithelial cobblestone monolayer appearance and contain dark brown pigment in their cytoplasm, which is known to be present in the human body only in melanocytes, keratinocytes, retinal and iris pigment epithelium (IPE). Melanocytes, however, are non-epithelial cells, and keratynocytes don't secrete but only accumulate melanin. The set of RPE-specific proteins—bestrophin, CRALBP, PEDF—present in these cells indicates that they are likely to be similar to RPE and not IPE. Another similarity is the behavior of isolated pigmented cells in culture, when little or no pigment was seen in proliferating cells but was retained in tightly packed epithelial islands or re-expressed in newly established cobblestone monolayer after the cells became quiescent. Such behavior was described for RPE cells in culture (reviewed by Zhao et al., 1997), and it was previously reported (Vinores et al., 1995) that a neuronal marker tubulin beta III was specifically localized in dedifferentiating RPE cells in vitro and not in the cells with the typical RPE morphology suggesting that it reflects the plasticity of RPE and its ability to dedifferentiate to a neural lineage. The inventors have observed the same pattern of tubulin beta III localization in primary and passaged cultures of RPE and RPE-like cells which can reflect a dedifferentiation of such cells in culture or indicate a separate population of cells committed to a neuronal fate, that were originally located next to pigmented cells through differentiation of hES cells in long-term cultures and could have been co-isolated with RPE-like cells.

In the growing optic vesicle RPE and the neural retina share the same bipotential neuroepithelial progenitor, and their fate was shown to be determined by Pax2, Pax6, and Mitf (Baumer et al., 2003), the latter being a target of the first two. Pax6 at earlier stages acts as an activator of proneural genes and is downregulated in the RPE in further development, remaining in amacrine and ganglion cells in mature retina (reviewed by Ashery-Padan and Gruss, 2001). In goldfish, it is also found in mitotically active progenitors of regenerating neurons (Hitchcock et al., 1996). The inventors have found that many of the RPE-like cells expressed mitf and Pax6 in a pattern similar to tubulin beta III and were found only in non-pigmented cells of non-epithelial morphology that surround pigmented epithelial islands in long term cultures or in cells with a "partial" RPE phenotype (lightly pigmented and loosely packed). In proliferating cells in recently passaged cultures all these markers were found nearly in every cell suggesting either a reversal of RPE-like cells to progenitor stage at the onset of proliferation or massive proliferation of retinal progenitors. Interestingly, in teratomas where islands of pigmented cells of epithelial morphology were also found, Pax6 was expressed in non-pigmented cells adjacent to pigmented regions (data not shown). Multiple studies have previously shown dedifferentiation of RPE in culture and their transdifferentiation into cells of neuronal phenotype (Reh and Gretton, 1987, Skaguchi et al., 1997, Vinores et al., 1995, Chen et al., 2003), neuronal, amacrine and photoreceptor cells (Zhao et al., 1995), glia (Skaguchi et al., 1997), neural retina (Galy et al., 2002), and to neuronal progenitors (Opaz and Dziak, 1993). Such progenitors can in turn coexist with mature RPE-like cells in culture or appear as a result of dedifferentiation of RPE-like cells. At the same time, cells of neural retina can transdifferentiate into RPE in vitro (Opas et al., 2001), so alternatively, tubulin beta III and Pax6 positive cells could represent a transient stage of such transdifferentiation of co-isolated neural cells or neural progenitors into RPE-like cells.

Differentiation of hES cells into RPE-like cells happened spontaneously when using methods described in the Examples below, and the inventors noticed that pigmented epithelial cells reliably appeared in cultures older than 6-8 weeks and their number progressed overtime—in 3-5 months cultures nearly every EB had a large pigmented region. In addition to the described hES lines, six more newly derived hES lines turned into RPE-like cells, which suggests that since neural fate is usually chosen by ES cells spontaneously, RPE-like cells can arise by default as an advanced stage of such pathway. It is also possible that in such long term cultures, where differentiating hES cells form a multi-layered environment, permissive and/or instructive differentiation signals come from extracellular matrix and growth factors produced by differentiating derivatives of hES cells. The model of differentiation of hES cells into RPE-like cells could be a useful tool to study how such microenvironment orchestrates RPE differentiation and transdifferentiation.

RPE plays an important role in photoreceptor maintenance, and various RPE malfunctions in vivo are associated with a number of vision-altering ailments, such as RPE detachment, displasia, athrophy, retinopathy, retinitis pigmentosa, macular dystrophy or degeneration, including age-related macular degeneration, which can result in photoreceptor damage and blindness. Because of its wound healing abilities, RPE has been extensively studied in application to transplantation therapy. It has been shown in several animal models and in humans (Gouras et al., 2002, Stanga et al., 2002, Binder et al., 2002, Schraermeyer et al., 2001, reviewed by Lund et al., 2001) that RPE transplantation has a good potential of vision restoration. Recently another prospective niche for RPE transplantation was proposed and even reached the phase of clinical trials: since these cells secrete dopamine, they could be used for treatment of Parkinson disease (Subramanian, 2001). However, even in an immune-privileged eye, there is a problem of graft rejection, hindering the progress of this approach if allogenic transplant is used. The other problem is the reliance on fetal tissue, as adult RPE has a very low proliferative potential.

As a source of immune compatible tissues, hES cells hold a promise for transplantation therapy, as the problem of immune rejection can be overcome with nuclear transfer technology. The new differentiation derivative of human ES cells, retinal pigment epithelium-like cells and the reliability and simplicity of such differentiation system may offer an attractive potential supply of RPE cells for transplantation.

EXAMPLES

Example 1

Spontaneous Differentiation into Pigmented Epithelial Cells in Long Term Cultures When hES cell cultures are allowed to overgrow on MEF in the absence of LIF, FGF and Plasmanate, they form a thick multilayer of cells. About 6 weeks later, dark islands of cells appear within the larger clusters (FIG. 1). These dark cells are easily seen with the naked eye and looked like "freckles" in a plate of cells as shown in FIG. 1A. At higher magnification these islands appear as tightly packed polygonal cells in a cobblestone monolayer, typical of epithelial cells, with brown pigment in the cytoplasm (FIG. 1C). There are differences in the amount of pigment in the cells with cells in the central part of the islands having the most pigment and those near the edges the least. (FIG. 1, E,F).

When hES cells form embryoid bodies (EB)—pigmented epithelial cells appear in about 1-2% of EBs in the first 6-8 weeks (FIG. 1B). Over time more and more EBs develop pigmented cells, and by 3 months nearly every EB had a pigmented epithelial region (FIG. 1D). Morphology of the cells in the pigmented regions of EBs was very similar to that of adherent cultures (FIG. 1D).

Example 2

Isolation and Culture of Pigmented Epithelial Cells

The inventors isolated pigmented epithelial cells from both adherent hES cell cultures and from EBs. Pigmented polygonal cells were digested with enzymes (trypsin, and/or collagenase, and/or dispase), and the cells from these pigmented islands were selectively picked with a glass capillary. Although care was taken to pick only pigmented cells, the population of isolated cells invariably contained some non-pigmented cells. After plating cells on gelatin or laminin for 1-2 days, the cells were considered to be primary cultures (P0).

Figure 2:
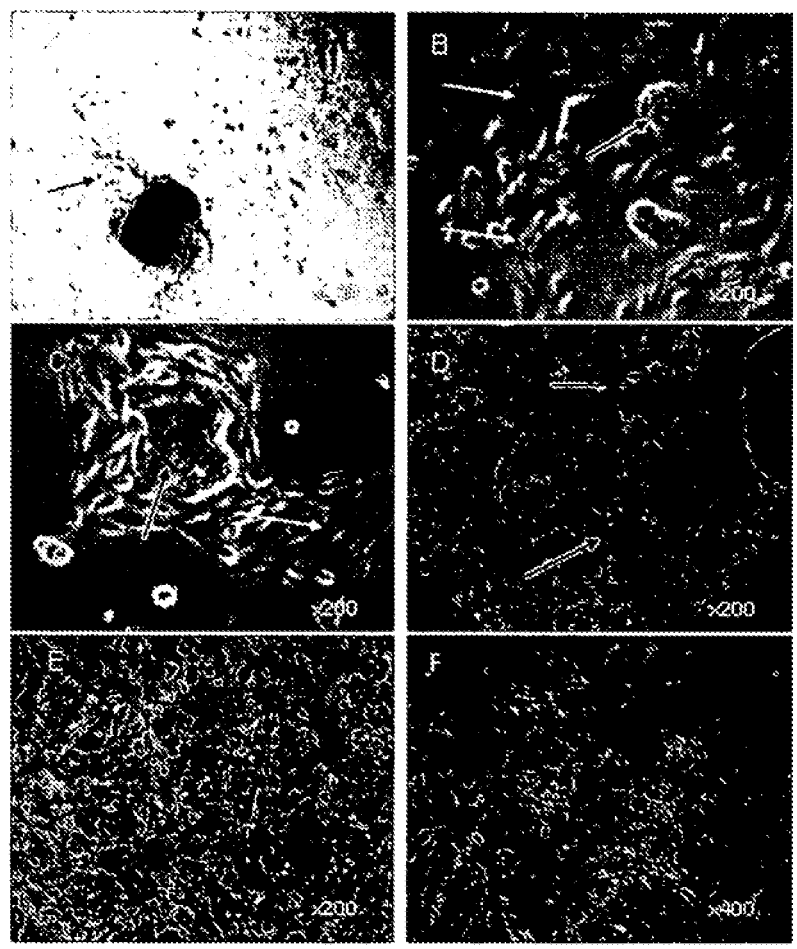
FIG. 2A is a photograph showing primary EB outgrowth, 1 week.
FIG. 2B is a photograph showing the primary culture of cells, isolated by trypsin, 1 week.
FIG. 2C is a photograph showing epithelial islet surrounded by proliferating cells.
FIG. 2D is a photograph showing the regain of pigmentation and epithelial morphology in 1 month old culture.
FIG. 2E is a photograph showing the culture after 3 passages, ×200 magnification.
FIG. 2F shows the same culture as in E, ×400 magnification, Hoffman microscopy. Black arrows point to pigmented cells, white arrows show outgrowing cells with no pigment.
Figure 3:
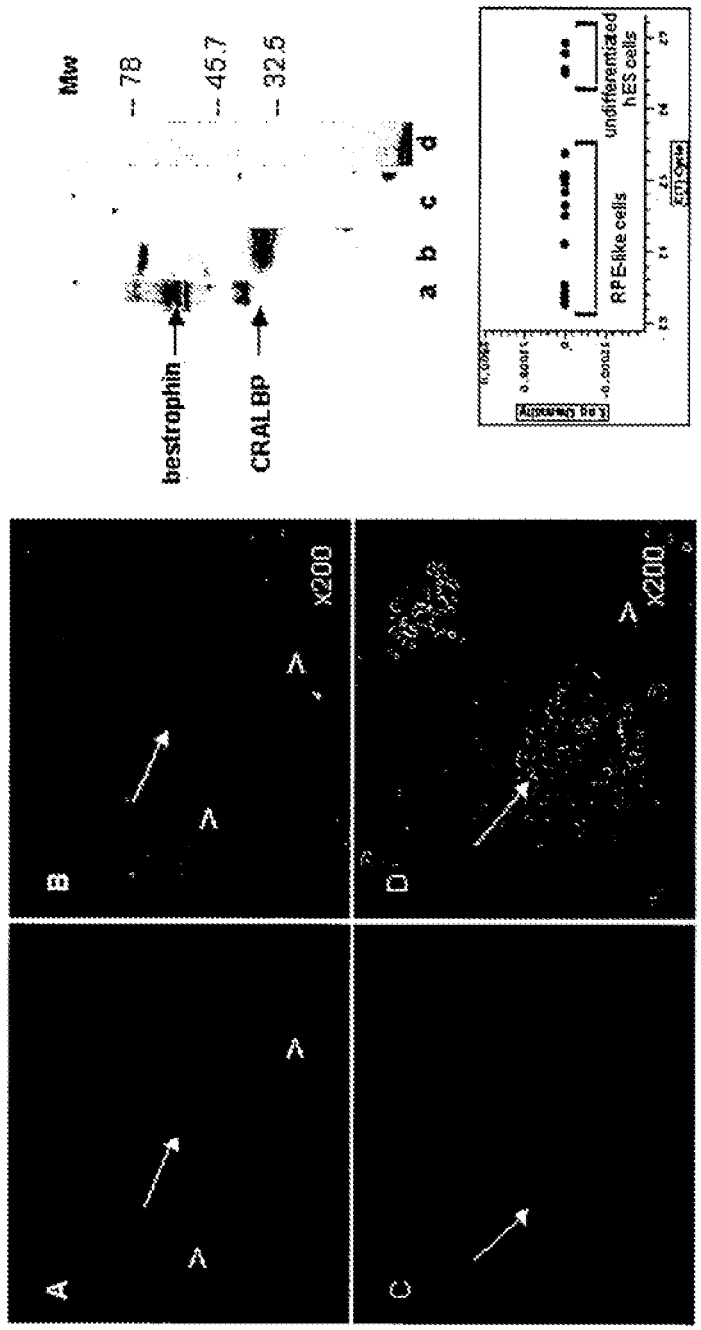
FIG. 3 Left Panel (A-D) and Right Panel is a series of photographs and one Graph—these show markers of RPE in hES cells-derived pigmented epithelial cells.

Primary cultures contained islands of pigmented polygonal cells as well as some single pigmented cells. After 3-4 days in culture, non-pigmented cells that seemed to have lost epithelial morphology (flatter and cells with lamellipodia) appeared at the periphery of some islands (FIG. 2). The number of such peripheral cells increased over time, suggesting that these cells were proliferating, and after 2 weeks most cells in the newly formed monolayer contained very little or no pigment. After continued culture, for another 2-3 weeks, pigmented epithelial cells began to reappear, visibly indistinguishable from those in the original cultures (FIG. 2).

Example 3

Detection of RPE Markers

Figure 4:
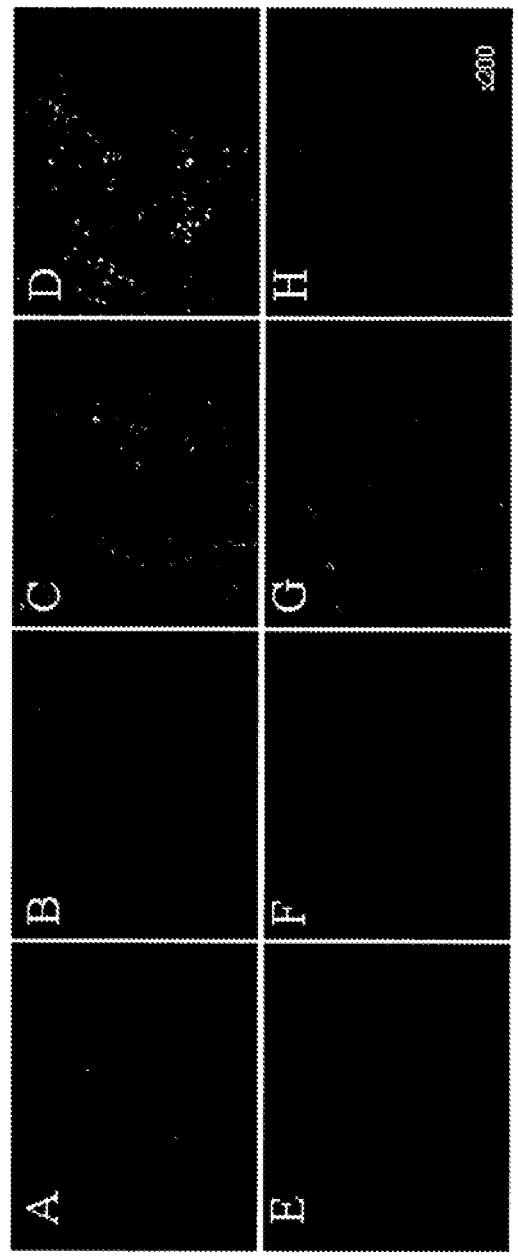
FIG. 4 shows photographs which demonstrate the expression of markers of Pax6 (FIG. 4A), Pax2 (FIG. 4E) and mitf (FIG. 4B, FIG. 4F) in RPE-like cells in long-term quiescent cultures.

The preliminary characterization of these differentiated human cells as RPE is based on their similarity to RPE cultures previously described; principally, their epithelial morphology and possession of pigment. There are three types of pigmented epithelial cells in human body: retinal and iris pigmented epithelium and keratinocytes, but the latter don't secrete pigment. The epithelial structure and cobblestone morphology are not shared by other pigmented cells, e.g. melanocytes. It is also noteworthy that RPE cells have been shown to lose and regain their pigment and epithelial morphology when grown in culture (Zhao 1997, Opas and Dziak, 1994), and the pigmented cells behaved in a similar manner, so to test the hypothesis that the ES derived cells may be RPE, they were stained with antibodies to known markers for RPE: bestrophin and CRALBP. FIG. 4 (left panel) shows membrane localization of bestrophin (A) and CRALBP (C), both are found in pigmented epithelial islands. Not all of the cells stain with these antibodies and intensity of staining correlated with pigment expression and "tightness" of colonies—the borders of each pigmented island where cells were larger and more loosely packed showed lower expression of both proteins.

To further characterize presumably RPE cells, analysis was performed on the expression of bestrophin, CRALBP by Western blotting. FIG. 4 (right panel) shows the bands, corresponding to bestrophin, 68 kD (a), CRALBP, 36 kD (b) in cell lysates. All these proteins were found in both primary cultures and subsequent passages.

Another known PRE marker, RPE65, was found in the RPE-like cells by real-time RT-PCR (FIG. 4, right panel, bottom), the PEDF ELISA assay showed the presence of PEDF in cell lysates of all presumed RPE cultures, and Western blot showed a band of approximately 48 kD (not shown). Detection of markers of neuronal and retinal progenitors in RPE-like cultures FIG. 4 shows localization of PAX-6, Pax2, mitf, and tubulin beta III in recently passaged and old cultures of hES cells-derived RPE. In proliferating cultures (day 3 after trypsinization, not shown) where RPE-like morphology of the proliferating cells is lost, nearly every cell showed the presence of mitf, Pax6, tubulin beta III and nestin (not shown). Pax2 was found only a small subset of cells which appeared mitf-negative, while there was a strong degree of co-localization of Pax6/mitf, mitf/tubulin beta III, and Pax6/tubulin beta III. In 21 days old quiescent cultures after pigmented epithelial islands were reestablished, groups of PAX-6 and mitf were found mostly in non-pigmented cells of non-epithelial morphology between pigmented epithelial islands (FIG. 4, A-C). and tubulin beta III had a similar pattern of distribution (not shown). However, there were populations of mitf-positive and Pax6-negative cells, located close to the periphery of pigmented islands (FIG. 4, A-C). Pax2 was found only in a very small subset of mitf-negative cells (FIG. 4, E-H). No presence of either of these proteins was ever detected in the cells of "mature" pigmented epithelial islands. However, these markers in cells that only had some RPE features were often visible, i.e. either looked epithelial but had no pigment or in certain single pigmented cells away from pigmented epithelial islands.

Example 4

Characterization of RPE-Like Cells Derived from hES Cell Lines H9 and ACT J-1 from Cyno-1 ES Cells and Derivation of RPE-Like Cells from Existing hES Cell Lines H1 and H7

An RPE-like cell line is expanded, tested for freezing and recovery, and characterized using the following methods and molecular markers of RPE cells: bestrophin and CRALBP by Western blot and immunofluorescence, PEDF by ELISA and Western blot, and REP65 by RT-PCR. The cells are injected in SCID mice with undifferentiated hES or Cyno-1 cells as a control to evaluate tumorigenicity. Karyotyping of RPE-like cells will be done by a clinical laboratory on a commercial basis. Characterization of the functional properties of RPE-like cells and studies of their transplantation potential are then carried out as otherwise described in this application and also using those techniques known to those skilled in the art.

Gene expression profiling experiments are done using Affymetrix human genome arrays. Gene expression is compared in RPE-like cells derived from ES cells and in retinal samples from autopsies. Several animal models can be used to verify the effectiveness of the transplanted RPE-like cells, including but not limited to, rhesus monkey, rat, and rabbit.

Example 5

Optimization of the Differentiation Culture System Ensuring High Yields of RPE-Like Cells ES cells are cultured on feeder cells or as embryoid bodies (EB) in the presence of bFGF, insulin, TGF-beta, IBMX, bmp-2, bmp-4 or their combinations, including stepwise addition. Alternatively, ES cells are grown on various extracellular matrix-coated plates (laminin, fibronectin, collagen I, collagen IV, Matrigel, etc.) in evaluating the role of ECM in RPE formation. Expression of molecular markers of early RPE progenitors (Pax6, Pax2, mitf) and of RPE cells (CRALBP, bestrophin, PEDF, REP65) are evaluated at various time intervals by real-time RT-PCR to verify and determine successful combinations of the above mentioned agents and stepwise procedure that produces enrichment in RPE-like cells or their progenitors. This approach can also be used to produce common progenitors of RPE and other eye tissues, such as photoreceptor or neural retina which can be isolated and further characterized for their differentiation potential and used in transplantation studies.

Example 6

Derivation of RPE and Other Eye Tissue Progenitors from Existing and New ES Cell Lines Using the data from the gene expression profiling, expression of the RPE progenitor markers will be correlated with the expression of the surface proteins in order to find a unique combination of surface markers for RPE progenitor cells. If such markers are found, antibodies to surface proteins can be used to isolate a pure population of RPE progenitors that can be then cultured and further differentiated in culture or used in transplantation studies to allow their differentiation after grafting.

If the data from the gene expression profiling experiments is insufficient, to isolate the RPE progenitors the following approach will be used. ES cells and RPE-like cells will be transfected with GFP under the control of a Pax6 promoter, and stable transfectants will be selected. From a culture of transfected differentiating ES cells or proliferating (dedifferentiated) RPE cells, GFP/Pax6-positive cells will be isolated by FACS and used as an antigen source for mouse injection to raise monoclonal antibodies to the surface molecules of Pax6 positive cells. Because Pax6 is present not only in RPE progenitors, screening will be done (by FACS) using several strategies: a) against proliferating RPE-like cells, b) against Pax2-positive RPE cells, c) against mitf-positive RPE cells. For b) and c) RPE cells will be transfected with GFP under the corresponding promoter; as a negative control, RPE or ES cells negative by these antigens will be used. After expansion of positive clones selected by all three strategies, antibodies will be tested against all types of cells used in screening and further analyzed: since this strategy can produce antibodies that recognize cell surface antigens specific and non-specific for RPE progenitors, the cells from differentiating total population of ES cells or of RPE cells selected with these antibodies will be assessed for molecular markers of RPE progenitors and for their ability to produce RPE.

Using the optimized defined stepwise procedures to produce RPE or other early progenitors of eye tissues and the antibodies to their unique surface markers, such progenitors will be isolated from differentiated ES cells and cultured in vitro. Their ability to differentiate into various tissues of the eye will be investigated using the strategy described in Aim 2.

Three ES cell lines that already produced RPE-like cells (H9, ACT J-1, Cyno-1), RPE-like cells will be used to continue to derive RPE-like cells and their progenitors as described in Aims 1 and 2, and H1 and H7 hES cell lines will be used to produce new RPE-like cell lines. After expansion and characterization for molecular markers of RPE, these lines will be single-cloned, and the resulting lines will be characterized as described in Aim 1. The lines meeting criteria for RPE cells will be used for transplantation studies. New human ES cell lines will be derived from unused IVF embryos, from donated oocytes, stimulated to develop without fertilization (parthenote), and from generated developing blastocysts obtained from donated oocytes with the application of nuclear transfer technology. RPE-like cells and common eye progenitors will be, derived from these lines using the approach in Aim 2, and the resulting lines will be characterized as in Aim 1. [Optional] new human ES cell lines will be derived in a virus-free system, characterized and submitted for clinical trials.

Example 7

Therapeutic Potential of RPE-Like Cells and Progenitors in Various Animal Models of Retinitis Pigmentosa & Macular Degeneration Primate ES cells are tested in cynomolgus monkeys (Macaques). Initially, vitrectomy surgery is performed and the cells are transplanted into the subretinal space of the animals. The first step is the transplantation of the cells in the suspension format after which a substrate or matrix is used to produce a monolayer transplantation. This can also be performed in immunosuppressed rabbits using cells derived from human ES-cells and also in various other animal models of retinitis pigmentosa, including rodents (rd mouse, RPE-65 knockout mouse, tubby-like mouse, RCS rat, cats (Abyssinian cat), and dogs (cone degeneration "cd" dog, progressive rod-cone degeneration "prcd" dog, early retinal degeneration "erd" dog, rod-cone dysplasia 1, 2 & 3 "rcd1, rcd2 & rcd3" dogs, photoreceptor dysplasia "pd" dog, and Briard "RPE-65) dog). Evaluation is performed using fluorescent angiography, histology (whether or not there is photoreceptor restoration and possibly ERG. Functional testing will also be carried out, including phagocytosis (photoreceptor fragments), vitamin A metabolism, tight junctions conductivity, and electron microscopy.

Example 8

Direct Differentiation of RPE Cells from Human Embryo-Derived Cells

Human blastocyst-staged embryos are plated in the presence of murine or chick embryo fibroblasts with or without immunosurgery to remove the trophectoderm or directly plates on extracellular matrix protein-coated tissue cultureware. Instead of culturing and passaging the cells to produce a human ES cell line, the cells are directly differentiated.

When hEDC cell cultures are allowed to overgrow on MEF in the absence of LIF, FGF and Plasmanate, they will form a thick multilayer of cells. (Alternate growth factors, media, and FBS can be used to alternate direct differentiation as is known to those skilled in the art.) About 6 weeks later, dark islands of cells will appear within the larger clusters. These dark cells are easily seen with the naked eye and looked like "freckles" in a plate of cells as shown in FIG. 5B. At higher magnification these islands appear as tightly packed polygonal cells in a cobblestone monolayer, typical of epithelial cells, with brown pigment in the cytoplasm (FIG. 5A). There are differences in the amount of pigment in the cells with cells in the central part of the islands having the most pigment and those near the edges the least. (FIG. 5B).

When hEDC cells are directly differentiated they may, though typically have not, formed embrioid bodies (EB). Pigmented epithelial cells appear in about 1-2% of these differentiated cells and/or EBs in the first 6-8 weeks. Over time more and more EBs develop pigmented cells, and by 3 months nearly every EB had a pigmented epithelial region. Morphology of the cells in the pigmented regions of EBs was very similar to that of adherent cultures.

Materials and Methods

MEF medium: high glucose DMEM, supplemented with 2 mM GlutaMAX I, and 500 u/ml Penicillin, 500 ug/ml streptomycin (all from Invitrogen) and 16% FCS (HyCLone). hES Cells Growth medium: knockout high glucose DMEM supplemented with 500 u/ml Penicillin, 500 ug/ml streptomycin, 1% non-essential amino acids solution, 2 mM GlutaMAX I, 0.1 mM beta-mercaptoethanol, 4 ng/ml bFGF (Invitrogen), 1-ng/ml human LIF (Chemicon, Temecula, Calif.), 8.4% of Serum Replacement (SR, Invitrogen) and 8.4% Plasmanate (Bayer). Derivation medium contained the same components as growth medium except that it had lower concentration of SR and Plasmanate (4.2% each) and 8.4% FCS and 2× concentration of human LIF and bFGF, as compared to growth medium. EB medium: same as growth medium except bFGF, LIF, and Plasmanate; the SR concentration was 13%. RPE medium: 50% EB medium and 50% MEF medium.

hES Cell Lines

The cell lines, hES 35, 36, 45, used for these studies were derived with modifications of previously reported procedures (Thomson et al., 1998, Reubinoff et al., 2000, Lanzendorf et al., 2001). Human frozen blastocysts (line hES35) or cleaved embryos (lines hES36 and hES45) were donated to the study, approved by two institutional review board, by couples who had completed their fertility treatment.

Differentiation experiments were performed with adherent hES cells or with embryoid bodies (EBs). For adherent differentiation, hES cells were allowed to overgrow on MEFs until the hES colonies lost their tight borders at which time the culture media was replaced with EB medium (usually, 8-10 days after passaging). The medium was changed every 1-2 days. For EB formation, hES cells were trypsinized and cultured in EB medium on low adherent plates (Costar).

Immunostaining

Cells were fixed with 2% paraformaldehyde, permeabilized with 0.1% NP-40 for localization of intracellular antigens, and blocked with 10% goat serum, 10% donkey serum (Jackson Immunoresearch Laboratories, West Grove, Pa.) in PBS (Invitrogen) for at least one hour. Incubation with primary antibodies was carried out overnight at 4° C., the secondary antibodies (Jackson Immunoresearch Laboratories, West Grove, Pa.) were added for one hour. Between all incubations specimens were washed with 0.1% Tween-20 (Sigma) in PBS 3-5 times, 10-15 minutes each wash. Specimens were mounted using Vectashield with DAPI (Vector Laboratories, Burlingame, Calif.) and observed under fluorescent microscope (Nikon). Localization of alkaline phosphatase was done either by Vector Red (Vector Laboratories, Burlingame, Calif.) to live cells or after the second wash during immunostaining according to manufacturer's instructions. Antibodies used: bestrophin (Novus Biologicals, Littleton, Colo.), anti-CRALBP antibody was a generous gift from Dr. Saari, University of Washington. Secondary antibodies were from Jackson Immunoresearch Laboratories, and Streptavidin-FITC was purchased from Amersham.

Isolation and Passaging of RPE-Like Cells

Adherent cultures of hES cells or EBs were rinsed with PBS twice and incubated in 0.25% Trypsin/1 mM EDTA (Invitrogen) at 37° C. until the monolayer loosened. Cells from the pigmented regions were scraped off with a glass capillary, transferred to MEF medium, centrifuged at 200×g, and plated onto gelatin-coated plates in RPE medium. The medium was changed after the cells attached (usually in 1-2 days) and every 5-7 days after that; the cells were passaged every 2-4 weeks with 0.05% Trypsin/0.53 mM EDTA (Invitrogen).

Western Blot and ELISA

Samples were prepared in Laemmli buffer (Laemmli, 1970), supplemented with 5% Mercaptoethanol and Protease Inhibitor Cocktail (Roche), boiled for 5 minutes and loaded onto a 8-16% gradient gel (Bio-Rad, Hercules, Calif.) using a Mini-Protean apparatus; the gels were run at 25-30 mA per gel; proteins were transferred to a 0.2 Nitrocellulose membrane (Schleicher and Shull, Keene, N.H.) at 20 volt overnight. Blots were briefly stained with Ponceau Red (Sigma) to visualize the bands, washed with Milli-Q water, and blocked for 1 hour with 5% non-fat dry milk in 0.1% TBST (Bio-Rad). Primary antibodies to bestrophin, CRALBP or PEDF (Chemicon) were added for 2 hours followed by three 15-minute washes with TBST; peroxidase-conjugated secondary antibodies were added for 1 hour, and the washes were repeated. Blots were detected using ECL system with SuperSignal reagent (Pierce). PEDF ELISA was performed on cell lysates using PEDF ELISA kit (Chemicon) according to manufacturer's protocol.

Real-Time RT-PCR

Total RNA was purified from differentiating ES cultures by a two-step procedure Crude RNA was isolated using Trizol reagent (Invitrogen) and further purified on RNeazy minicolumns (Qiagen). The levels of RPE65 transcripts were monitored by real-time PCR using a commercial primer set for RPE65 detection (Assay on Demand # Hs00165642_m1, Applied Biosystems) and Quantitect Probe RT-PCR reagents (Qiagen), according to the manufacturer's (Qiagen) protocol.

Derivation and Characterization of Undifferentiated hES Cell Lines

Two female one male hES cell lines were used in these studies. Details on the derivation of these hES lines are reported elsewhere. All lines have been passaged more than 50 times during which time they maintain an undifferentiated colony morphology, high alkaline phosphatase activity, and express Oct-4, SSEA-3, SSEA-4, TRA I-60, and TRA I-81 (data not shown). Two lines have normal karyotype (hES36, hES35), while there were both normal and aneuploid subpopulations in hES45. Upon spontaneous differentiation both in vitro and in teratomas all lines expressed the markers of three germ layers—muscle actin, alpha-fetoprotein, and tubulin beta III.

Example 9

Use of Transcript Genomics to Identify Normal Differentiated Cells Differentiated Ex Vivo Transcriptomics—hES-cell derivatives are likely to play an important role in the future of regenerative medicine. Qualitative assessment of these and other stem cell derivatives remains a challenge that could be approached using functional genomics. We compared the transcriptional profile of hES-RPE vs. its in vivo counterpart, fetal RPE cells, which have been extensively researched for its transplantation value. Both profiles were then compared with previously published (Rogojina et al., 2003) transcriptomics data on human RPE cell lines.

The gene expression profile of our data set was compared to two human RPE cell lines (non-transformed ARPE-19 and transformed D407, Rogojina et al., 2003) to determine whether hES-RPE have similar global transcriptional profiles. To account for common housekeeping genes expressed in all cells, we used publicly available Affymetrix data sets from undifferentiated hES cells (H1 line, h1-hES,—sato et al., 2003) and bronchial epithelial cells (BE, Wright et al., 2004) as a control based on its common epithelial origin that would allow to exclude common housekeeping and epithelial genes and identify RPE-specific genes.

There were similarities and differences between hES-RPE, hES-RPE-TD, ARPE-19, D407. The similarities were further demonstrated by analyzing the exclusive intersection between those genes present in hES-RPE/ARPE-19 but not in BE (1026 genes). To account for background, we compared this to the exclusive intersection of genes present in BE/hES-RPE, but not ARPE-19 (186 genes), which results in a five- to six-fold greater similarity in hES-RPE and ARPE-19 when compared to BE. D407/ARPE19 appear to lose RPE specific genes such as RPE65, Bestrophin, CRALBP, PEDF, which is typical of long-term passaged cells (FIG. 6). Further data mining revealed known RPE specific ontologies such as melanin biosynthesis, vision, retinol-binding, only in fetal RPE and ES-RPE but not ARPE19.

Comparison of hES-RPE, ARPE-19 and D407 to their in vivo counterpart, freshly isolated human fetal RPE (feRPE), was in concordance with our previous data, demonstrating that the transcriptional identity of hES-RPE to human feRPE is significantly greater than D407 to fe RPE (2.3 fold difference—849 genes/373 genes) and ARPE-19 to feRPE (1.6 fold difference—588 genes/364 genes (FIG. 5c/5d). The RPE specific markers identified above, which were only present in hES-RPE and not in ARPE-19 or D407 were also present in feRPE, demonstrating a higher similarity of hES-RPE to its in vivo counterpart than of the cultured RPE lines.

Seven-hundred-and-eighty-four genes present in hES-RPE were absent in feRPE and ARPE-19 data sets. Since the retention of "stemness" genes could potentially cause transformation of hES derivatives into malignant teratomas if transplanted into patients, we created a conservative potential "stemnness" genes data using currently available Affymetrix microarray data sets Abeyta et. al 2004 Sato 2003). This resulted in a list of 3806 genes present in all 12 data sets (including common housekeeping genes). j Only 36 of the 784 genes present in the hES-RPE dats et but not feRPE-ARPE-19 were common to the 3806 potential stemness genes. None of these were known stemness genes such as Oct4, Sox2, TDGF1.

Example 10

Use of RPE Cells for Treatment of Parkinson's Disease hRPE can be used as an alternative source of cells for cell therapy of Parkinson's Disease because they secrete L-DOPA. Studies have showed that such cells attached to gelatin-coated microcarriers can be successfully transplanted in hemiparkinsonian monkeys and produced notable improvements (10-50) thousand cells per target), and in FDA-approved trial started in 2000 the patients received hRPE intrastriatial transplants without adverse effects. One of the many advantages to the use of hES cell-derived RPE is that it circumvents the shortage of donor eye tissue. It also facilitates the use of gene therapy.

Other Embodiments

From the foregoing description, it will be apparent that variations and modifications may be made to the invention described herein to adopt it to various usages and conditions.

We claim:
1. A method for the differentiation of human embryonic stem (hES) cells, said method comprising:
    a) culturing a multilayer of cells, produced from hES cells, for a sufficient time for the appearance of pigmented cells comprising brown pigment dispersed in their cytoplasm, under conditions that do not maintain stem cells in an undifferentiated state, wherein the hES cells are stem cells that express Oct-4, alkaline phosphatase, SSEA-3, SSEA-4, TRA-I-60 and TRA-I-81; and
    b) isolating and culturing the pigmented cells under adherent conditions to form a population of cells that expresses bestrophin, CRALBP, PEDF1 and RPE65.

2. The method of claim 1, wherein the population of cells in (b) comprises cells having a cobblestone, polygonal appearance.

3. The method of claim 2, wherein the population of cells in (b) comprises cells that are tightly packed.

4. The method of claim 1, further comprising isolating the population of cells in (b) as a suspension.

5. The method of claim 1, further comprising isolating the population of cells in (b) as a monolayer.

6. The method of claim 1, further comprising isolating and placing the population of cells in (b) on a matrix or a substrate.

7. The method of claim 1, wherein the multilayer of cells is produced by allowing hES cells to overgrow and form the multilayer of cells.

8. The method of claim 1, wherein isolating the pigmented cells comprises contacting the pigmented cells with one or more enzymes selected from the group consisting of trypsin, collagenase and dispase.

9. The method of claim 1, further comprising isolating and transplanting the population of cells into an eye of a patient to treat a retinal disease or condition.

10. The method of claim 9, wherein the population of cells is transplanted by vitrectomy surgery into the subretinal space of the eye of the patient.

11. The method of claim 9, wherein the patient has a retinal disease or condition selected from the group consisting of retinitis pigmentosa, retinal detachment, retinal dysplasia, retinal atrophy, retinopathy, macular dystrophy, cone dystrophy, cone-rod dystrophy, Malattia Leventinese, Doyne honeycomb dystrophy, Sorsby's dystrophy, pattern/butterfly dystrophies, Best vitelliform dystrophy, North Carolina dystrophy, central areolar choroidal dystrophy, angioid streaks, or a toxic maculopathy.

12. The method of claim 9, wherein the patient has Stargardt disease, pathologic myopia, retinitis pigmentosa, or macular degeneration.

13. The method of claim 9, wherein the patient has age-related macular degeneration.

14. The method of claim 9, wherein the population of cells is cryopreserved and then thawed prior to being transplanted into the patient.

15. The method of claim 9, wherein the population of cells is in a suspension.

16. The method of claim 9, wherein the population of cells is a monolayer.

17. The method of claim 9, wherein the population of cells is on a matrix or a substrate.

* * * * *